United States Patent
Singh et al.

(10) Patent No.: US 10,940,290 B2
(45) Date of Patent: Mar. 9, 2021

(54) FLUID DELIVERY SYSTEMS AND METHODS

(71) Applicant: ALCYONE LIFESCIENCES, INC., Lowell, MA (US)

(72) Inventors: Deep Arjun Singh, Cambridge, MA (US); Jonathan Freund, Woburn, MA (US); P J Anand, Lowell, MA (US); Thomas T. Washburn, Lancaster, MA (US); Andrew William East, Arlington, MA (US); Elsa Chi Abruzzo, Paradise Valley, AZ (US)

(73) Assignee: ALCYONE LIFESCIENCES, INC., Lowell, MA (US)

( * ) Notice: Subject to any disclaimer, the term of this patent is extended or adjusted under 35 U.S.C. 154(b) by 0 days.

(21) Appl. No.: 16/113,955

(22) Filed: Aug. 27, 2018

(65) Prior Publication Data
US 2020/0061337 A1    Feb. 27, 2020

(51) Int. Cl.
  *A61M 25/01*  (2006.01)
  *C12N 15/861* (2006.01)
  *A61M 25/02*  (2006.01)
  *A61B 5/00*   (2006.01)

(52) U.S. Cl.
  CPC ........ *A61M 25/0102* (2013.01); *A61M 25/02* (2013.01); *C12N 15/861* (2013.01); *A61B 5/686* (2013.01); *A61M 2202/0464* (2013.01); *A61M 2210/1003* (2013.01)

(58) Field of Classification Search
  CPC .......... A61M 25/0102; A61M 25/0105; A61M 25/0108; A61M 25/02; A61M 25/0286; A61M 2202/0464; A61M 2210/1003; A61M 25/0015
  See application file for complete search history.

(56) References Cited

U.S. PATENT DOCUMENTS

| | | | |
|---|---|---|---|
| 4,557,721 A * | 12/1985 | Hoven .............. | A61M 27/006 137/510 |
| 4,929,236 A | 5/1990 | Sampson | |
| 5,185,003 A | 2/1993 | Brethauer | |

(Continued)

OTHER PUBLICATIONS

International Application No. PCT/US2019/048096, International Search Report and Written Opinion, dated Dec. 26, 2019.

(Continued)

*Primary Examiner* — Kevin C Sirmons
*Assistant Examiner* — Tezita Z Watts
(74) *Attorney, Agent, or Firm* — Marshall, Gerstein & Borun LLP

(57) ABSTRACT

Fluid delivery systems and methods of delivering an agent and treating a disorder are disclosed that include a subcutaneously implantable port having a body defining a chamber with an open top and a delivery opening and a septum coupled to the body to extend over the open top of the chamber. The systems and methods can further include an intrathecal catheter having an proximal end configured to be coupled to the port and fluidly coupled to the delivery opening of the chamber and a plug having a body with a passage to receive the intrathecal catheter therethrough. The plug can be configured to be inserted into the fascia to protect against leakage of cerebrospinal fluid.

28 Claims, 25 Drawing Sheets

(56) References Cited

U.S. PATENT DOCUMENTS

| | | | |
|---|---|---|---|
| 5,704,926 A * | 1/1998 | Sutton | A61M 25/005 604/264 |
| 5,954,687 A | 9/1999 | Baudino | |
| 6,039,712 A | 3/2000 | Fogarty et al. | |
| 6,193,685 B1 * | 2/2001 | Goodin | A61M 25/1006 604/102.01 |
| 6,609,020 B2 | 8/2003 | Gill | |
| 6,962,580 B2 | 11/2005 | Adams et al. | |
| 7,131,962 B1 | 11/2006 | Estabrook et al. | |
| 8,641,688 B2 | 2/2014 | Powers et al. | |
| 8,932,271 B2 | 1/2015 | Hamatake et al. | |
| 8,974,422 B2 * | 3/2015 | Gill | A61M 39/0247 604/175 |
| 9,433,764 B2 * | 9/2016 | East | A61M 39/225 |
| 9,682,193 B2 | 6/2017 | Anand et al. | |
| 10,052,470 B2 | 8/2018 | Powers et al. | |
| 10,052,471 B2 | 8/2018 | Hamatake et al. | |
| 2005/0137579 A1 * | 6/2005 | Heruth | A61M 5/14276 604/536 |
| 2006/0264898 A1 | 11/2006 | Beasley et al. | |
| 2007/0255237 A1 | 11/2007 | Lobl et al. | |
| 2008/0114308 A1 | 5/2008 | di Palma et al. | |
| 2008/0275401 A1 * | 11/2008 | Sage | A61M 25/0612 604/175 |
| 2008/0319405 A1 | 12/2008 | Bizup | |
| 2012/0022502 A1 * | 1/2012 | Adams | A61M 25/005 604/526 |
| 2012/0232624 A1 * | 9/2012 | Sage | A61N 1/05 607/116 |
| 2013/0035660 A1 * | 2/2013 | Anand | A61M 5/16804 604/500 |
| 2015/0025478 A1 | 1/2015 | Hibdon et al. | |
| 2015/0165166 A1 * | 6/2015 | Gill | A61M 25/0662 604/500 |
| 2016/0122759 A1 * | 5/2016 | Kasperkovitz | A61K 9/5123 424/489 |
| 2017/0105927 A1 * | 4/2017 | Thorne | A61K 9/0004 |
| 2017/0258996 A1 | 9/2017 | Anand et al. | |
| 2018/0028761 A1 | 2/2018 | Anand et al. | |
| 2018/0064919 A1 | 3/2018 | East et al. | |
| 2018/0185058 A1 | 7/2018 | Anand et al. | |
| 2018/0214679 A1 | 8/2018 | Jho | |
| 2018/0214680 A1 | 8/2018 | Jho et al. | |

OTHER PUBLICATIONS

U.S. Appl. No. 16/113,943, Final Office Action, dated Jul. 1, 2019.
U.S. Appl. No. 16/113,943, Nonfinal Office Action, dated Dec. 26, 2019.
U.S. Appl. No. 16/113,943, filed Aug. 27, 2018.
Non-Final Office Action corresponding to U.S. Appl. No. 16/113,943 dated Feb. 11, 2019.

* cited by examiner

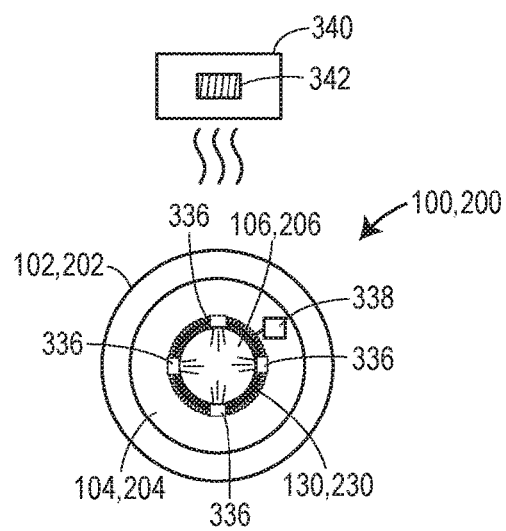
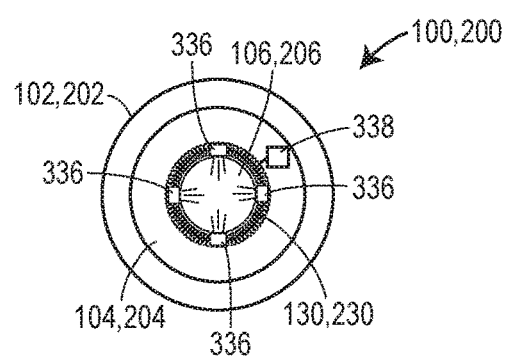
FIG. 18    FIG. 19
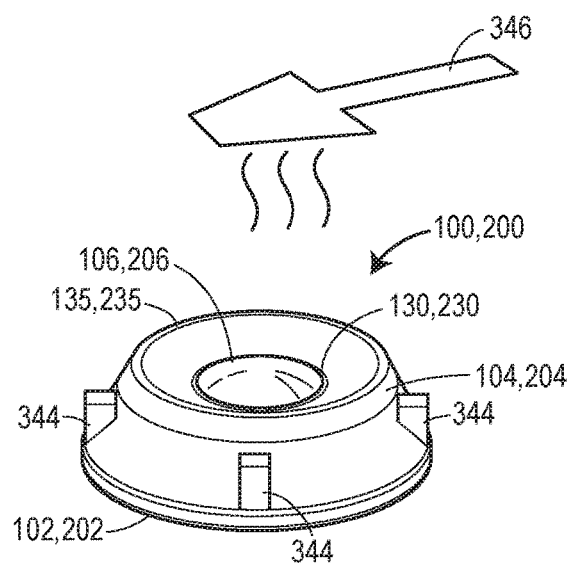
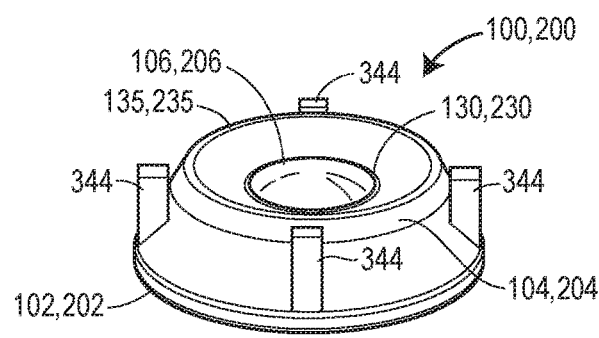
FIG. 20    FIG. 21

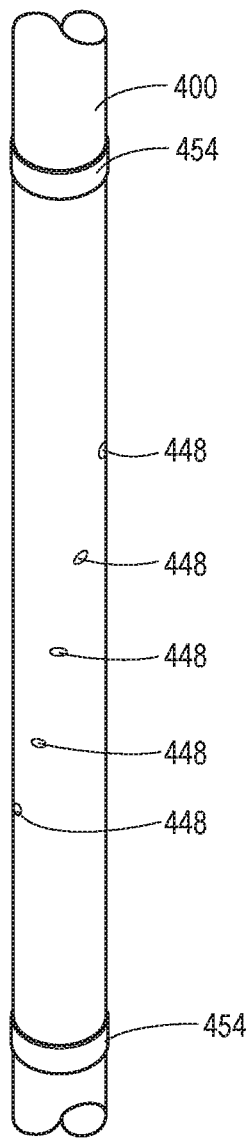
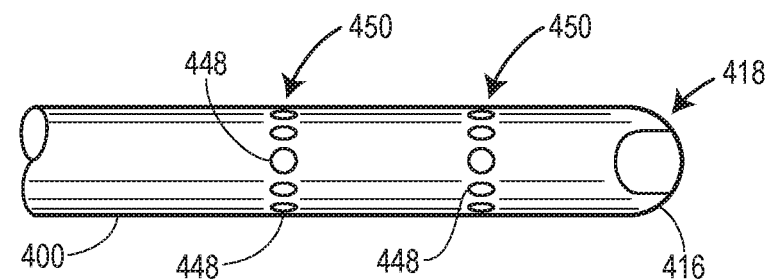
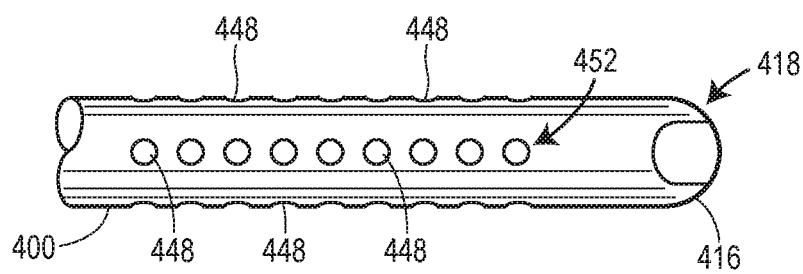
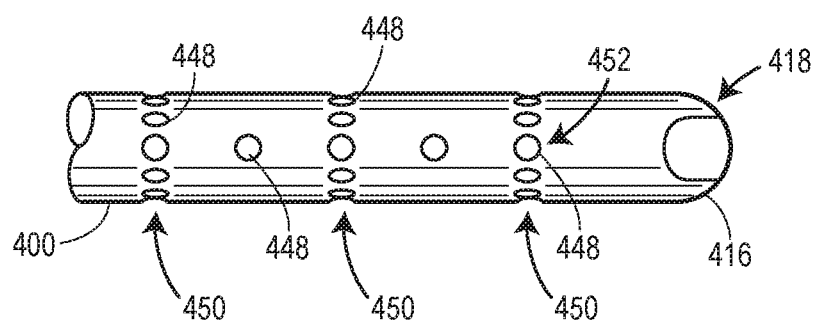
FIG. 38A
FIG. 38B
FIG. 38C
FIG. 38D

FLUID DELIVERY SYSTEMS AND METHODS

FIELD OF THE DISCLOSURE

The present disclosure generally relates to fluid delivery systems and, more particularly, to intrathecal fluid delivery systems.

BACKGROUND

Intrathecal administration is a valuable tool for introducing therapeutic agents into the cerebral spinal fluid (CSF), which allows distribution throughout the central nervous system. Indeed, therapeutics administered to CSF are distributed to the brain and spinal cord, thereby avoiding potential delivery issues through the blood-brain barrier. Most drugs delivered to the CSF require multiple administrations, requiring at least periodic access to the intrathecal space over the course of a treatment regimen. Some individuals are unable to receive medication via lumbar puncture due to anatomical barriers, such as spinal deformities, and/or surgical interventions, such as implantation of stabilizing rods and spondylosis. Bone fusions, sharp angles, and instrumentation in these individuals complicate or prevent direct lumbar puncture entry into the intrathecal space because there is no space between the bones to allow safe puncture of the dura. In these patients, extraordinary means are often required to achieve intrathecal access; for example, an oscillating drill may be required to bore through the bone mass or a laminectomy procedure may be required, which heightens the risk associated with intrathecal administration. There remains a need in the art for a delivery system that allows repeated administration of substances to the intrathecal space.

SUMMARY

In accordance with one aspect, a fluid delivery system is disclosed that includes a port that is implantable to a subcutaneous location. The port includes a body that defines a chamber having an open top and a delivery opening and a septum coupled to the body to extend over the open top of the chamber. The fluid delivery system further includes an intrathecal catheter that has a proximal end that is configured to be coupled to the port and fluidly coupled to the delivery opening of the chamber, a distal end, a central passage extending between the proximal end and the distal end, and a distal outlet in the distal end. The fluid delivery system further includes a plug that has a body with a passage to receive the intrathecal catheter therethrough, where the plug is configured to be inserted into the fascia to protect against leakage of cerebrospinal fluid.

According to some forms, that fluid delivery system can include one or more of the following aspects: the intrathecal catheter can include a plurality of radially oriented outlets, where the plurality of radially oriented outlets can be disposed along an axial length of the intrathecal catheter in a spiral configuration, the plurality of radially oriented outlets can include at least one of: one or more rings of outlets disposed within a plane normal to an axial length of the intrathecal catheter or a plurality of outlets aligned and spaced from one another along the axial length of the intrathecal catheter.

According to some forms, the fluid delivery system can include one or more of the following aspects: the intrathecal catheter can be radiopaque; the intrathecal catheter can include radiopaque markings at one or more of: adjacent to the distal end, above a start of the plurality of radially oriented outlets, or below an end of the radially oriented outlets; at least a portion of the intrathecal catheter can have a 3 layer construction including an inner lumen, a reinforcement layer, and an outer jacket; the distal end of the intrathecal catheter can include an atraumatic tip allowing implantation without damaging or exiting the intrathecal space; the central passage can include a choked portion adjacent to the distal outlet to create a venturi effect with fluid being dispensed through the distal outlet; the distal end of the intrathecal catheter can include one or more side passages that fluidly couple the central passage to an exterior of the intrathecal catheter to draw in fluid from the exterior of the intrathecal catheter and provide flow mass amplification to fluid being dispensed through the distal outlet; the distal outlet can have a smaller diameter than an inner diameter of the central passage of the intrathecal catheter adjacent to the distal outlet; the central passage can have an increased inner diameter portion in the distal end of the intrathecal catheter relative to an intermediate portion of the central passage, where the increased inner diameter portion extends to the distal outlet; the intrathecal catheter can have an outer diameter in the range of about 0.25 mm to about 1.5 mm; the intrathecal catheter can include an outwardly tapered portion adjacent to the proximal end thereof, where the outwardly tapered portion is configured to engage the dura over the catheter opening therein; the proximal end of the intrathecal catheter can include a reinforcement material increasing the hoop strength of the proximal end, where the reinforcement material includes one or more of: a plurality of rings embedded within the intrathecal catheter proximal end, a coil embedded within the intrathecal catheter proximal end, a polymer tube embedded within the intrathecal catheter proximal end, or a braided material embedded within the intrathecal catheter proximal end.

In accordance with a second aspect, a method of delivering an agent to a patient that has undergone a spinal stabilization or fusion procedure or suffers from a spinal deformity is disclosed that includes implanting a fluid delivery system in the patient such that a catheter of the fluid delivery system is disposed within the patient's intrathecal space, the catheter characterized by a catheter body having an outer diameter in the range of about 0.25 mm to 1.5 mm and a composite, kink-resistant structure, and the fluid delivery system further comprising a plug having a body with a passage to receive the catheter body therethrough, the plug configured to be inserted into the fascia to protect against leakage of cerebrospinal fluid; and releasing the agent via the catheter into the intrathecal space.

In accordance with a third aspect, a method of treating a disorder selected from the group consisting of Huntington's disease, Spinal Muscular Atrophy (SMA), survival motor neuron (SMN) deficiency, amyotrophic lateral sclerosis (ALS), Angelman's Syndrome, Dravet Syndrome, Alzheimer's disease, progressive supranuclear palsy (PSP), frontotemporal dementia (FTD), Parkinson's Disease, central nervous system (CNS) lymphoma, and Leptomeningeal Cancer in a patient in need thereof is disclosed that includes implanting a fluid delivery system in the patient such that a catheter of the fluid delivery system is disposed within the patient's intrathecal space, the catheter characterized by a catheter body having an outer diameter in the range of about 0.25 mm to 1.5 mm and a composite, kink-resistant structure, and the fluid delivery system further comprising a plug having a body with a passage to receive the catheter body therethrough, the plug configured to be inserted into the fascia to protect against leakage of cerebrospinal fluid; and releasing a therapeutic agent via the catheter into the intrathecal space such that the disorder is treated.

In accordance with a third aspect, a fluid delivery system is disclosed that includes a port implantable to a subcutaneous location. A body of the port defines a chamber having an open top and a delivery opening, a septum of the port is disposed on the body and includes a lower surface that extends over the open top of the chamber and an opposite, upper surface, and a cap of the port defines an opening extending therethrough. The cap is configured to be coupled to the body to secure the septum within the port with the opening providing needle access to the septum and the cap includes a downwardly tapered surface extending around the opening and configured to direct a needle towards the upper surface of the septum. The fluid delivery system further includes a catheter connection portion of the body.

In accordance with a fourth aspect, a fluid delivery system is described that includes a port that is implantable to a subcutaneous location secured to a bony structure of a patient. A body of the port defines a chamber that has an open top and a delivery opening, a septum of the port is disposed on the body to extend over the open top of the chamber, and a cap of the port is configured to be coupled to the body to secure the septum within the port. The cap defines an opening extending therethrough, such that with the cap coupled to the body, the opening provides needle access to the septum.

According to some forms, the above fluid delivery systems can include one or more of the following features: one or more of the body, septum, cap, or catheter can be radiopaque; the cap can include a downwardly tapered surface extending around the opening; the port can include raised protrusions that are configured to provide palpatory feedback; the port can include outwardly protruding suture plugs that are configured to provide palpatory feedback; the port can include a raised lip that extends around the septum, and that system can include a guide tool that has a profile that is configured to mate with the raised lip through tissue to provide an external location detector for the septum; the port can include an actuator having a movable portion to provide at least one of tactile or visual feedback in response to actuation; piezoelectric crystals that are mounted to the port and configured to vibrate in response to an electric field introduced by an external instrument and, optionally, one or more LEDs mounted to the port and electrically coupled to the piezoelectric crystals to energize in response to palpation of the piezoelectric crystals; one or more magnets distributed about the septum within the port, and the system can include a metallic external guide that is attracted to the one or more magnets through tissue to provide a guide for needle access to the septum; the port can include metallic portions that are distributed about the septum, and that system can include a magnetic ring that is configured to magnetically couple to the metallic portions through tissue to provide a guide for needle access to the septum; the body and cap can include a combination of metallic and non-metallic components such that the body and cap are distinguishable under imaging; a plurality of LEDs mounted to the port to provide illumination through tissue of at least one of the septum or around the septum; one or more sensors disposed within the port to provide one or more of: distance, alignment, orientation, targeting, or location data relative to an external device in communication with the one or more sensors; the septum can include one or more internal cavities filled with an aqueous gel material detectable by ultrasound; the body can include a side opening to the chamber for a stylet and the system can further include a septum mounted within the side opening; or a therapeutic dose impregnated or pre-loaded in the port.

According to additional forms, the fluid delivery system can further include a catheter that has a proximal end configured to be coupled to the body to be fluidly coupled to the delivery opening of the chamber and a distal end having an outlet. According to further forms, the catheter can include radially oriented outlets disposed along a length thereof in a spiral configuration; the catheter can include radiopaque markings at one or more of: adjacent to the distal tip, above a start of the spiral configuration, below an end of the spiral configuration; the catheter can have a 3 layer construction including an inner lumen, a reinforcement layer, and an outer jacket; the distal end of the catheter can include an atraumatic tip; or the distal end of the catheter can include side passages for flow mass amplification.

According to further forms, a catheter can be coupled to the port by any of the following: the delivery opening can include a cylindrical cavity having a connection portion, which can be one of a threaded portion, a snap-fit recess, or a luer lock recess, and the system can include a gasket disposed over the catheter proximal end and a fastener configured to engage the connection portion of the cylindrical cavity to compress the compression member to secure the catheter proximal end within the cylindrical cavity; the port can include an outlet tube extending from the delivery opening of the chamber, the catheter proximal end can have an annular configuration sized to have the outlet tube inserted therein and the system can further include a compression member, which can be one of a compression spring, a compression fitting, or an o-ring, disposed around the catheter proximal end and outlet tube to secure the catheter to the port; the port can include an outlet tube extending from the delivery opening of the chamber, the catheter proximal end and the outlet tube can have a lap joint connection, and the system can further include a clamping member disposed over the lap joint connection to create fluid tight seal.

According to any of the above forms, the fluid delivery system can further include one or more dosages of a therapeutic agent, as described further below.

In accordance with a fifth aspect, a method for implanting a fluid delivery port and a catheter in an intrathecal space of a patient is described herein that includes mounting the port to a bony structure within a subcutaneous space of the patient, disposing a distal tip of the catheter in the intrathecal space, tunneling a proximal end of the catheter under the skin of the patient to the port, and connecting the proximal end of the catheter to the port.

According to some forms, connecting the proximal end of the catheter to the port can include inserting the proximal end of the catheter into an annular gasket, inserting the proximal end of the catheter and the compression member into a cylindrical outlet cavity of the port, and inserting a fastener into the cylindrical outlet cavity of the port to longitudinally compress the gasket and secure the proximal end of the catheter to the port.

According to other forms, connecting the proximal end of the catheter to the port can include disposing the proximal end of the catheter over an outlet tube of the port and securing the catheter to the outlet tube with a compression member disposed over the catheter.

In accordance with a sixth aspect, a method for delivering a composition, such as a composition comprising a therapeutic agent, to an intrathecal space of a patient is described that includes locating a port secured in a subcutaneous position within a patient through tissue of the patient, inserting a distal tip of a needle through the tissue of the patient, through a septum of the port, and into a chamber of the port, dispensing the composition into the chamber, and distributing the composition into the intrathecal space of the patient through a catheter fluidly coupled to the port.

According to some forms, locating the port can include one or more of the following: imaging radiopaque portions of the port; palpating raised protrusions of the port; palpating suture plugs coupled to the port; mating a guide tool with a raised lip of the port; actuating an actuator having a movable portion providing at least one of tactile or visual feedback; emitting an electric field to vibrate piezoelectric crystals mounted to the port; attracting a metallic guide to one or more magnets distributed about the septum within the port; attracting a magnetic guide to one or more metallic portions distributed about the septum of the port; imaging metallic and non-metallic components of the port; illuminating one or more LEDs mounted to the port; communicating with one or more sensors disposed within the port with an external device to provide one or more of: distance, alignment, orientation, targeting, or location data relative to the external device; or detecting an aqueous gel material within the port by ultrasound.

According to some forms, dispensing the composition into the chamber can include dispensing one or more therapeutic agents described further below.

BRIEF DESCRIPTION OF THE DRAWINGS

The above needs are at least partially met through provision of the embodiments described in the following detailed description, particularly when studied in conjunction with the drawings, wherein:

FIG. 18 is a top plan view of a sixth example port for a fluid delivery system having location feedback features in accordance with various embodiments;

FIG. 19 is a top plan view of a seventh example port for a fluid delivery system having location feedback features in accordance with various embodiments;

FIG. 20 is a top plan view of a eighth example port for a fluid delivery system having location feedback features with an external device in accordance with various embodiments;

FIG. 21 is a side elevational view of the port of FIG. 20 in accordance with various embodiments;

FIG. 38a is a sectional view of an intermediate portion of the catheter of FIG. 34 showing first example radial outlets in accordance with various embodiments;

FIG. 38b is a sectional view of a portion of a catheter showing second example radial outlets in accordance with various embodiments;

FIG. 38c is a sectional view of a portion of a catheter showing third example radial outlets in accordance with various embodiments;

FIG. 38d is a sectional view of a portion of a catheter showing fourth example radial outlets in accordance with various embodiments;

DETAILED DESCRIPTION

The fluid delivery devices, systems and methods described herein include a sterile, implantable intrathecal catheter and subcutaneous port. The fluid delivery devices are designed to facilitate intrathecal access in patients with normal spines, as well as patients with spinal deformities and/or instrumentation for whom intrathecal access, and the associated fluid administration and sampling, via lumbar puncture (LP) is complicated or not possible. By utilizing the devices, systems, and methods provided, the need for repeat anesthesia and surgery each time intrathecal access is needed in these patients can be avoided.

The fluid delivery systems can be used to administer fluids (optionally including one or more therapeutic agents) to patients by means of manual bolus injection, standard syringe pump or Pulsar auto-injector pump. Therapeutics approved for bolus intrathecal administration would be infused into the patient through the subcutaneous port by palpating the port to identify the septum, and accessing the septum with a needle, such as a standard non-coring Huber needle. Additionally, or alternatively, the system can include a non-invasive detection guide. In some versions, the systems can utilize magnetic components, sensors, light sources, and/or transmitters to provide location aid to a clinician.

Figure 1:
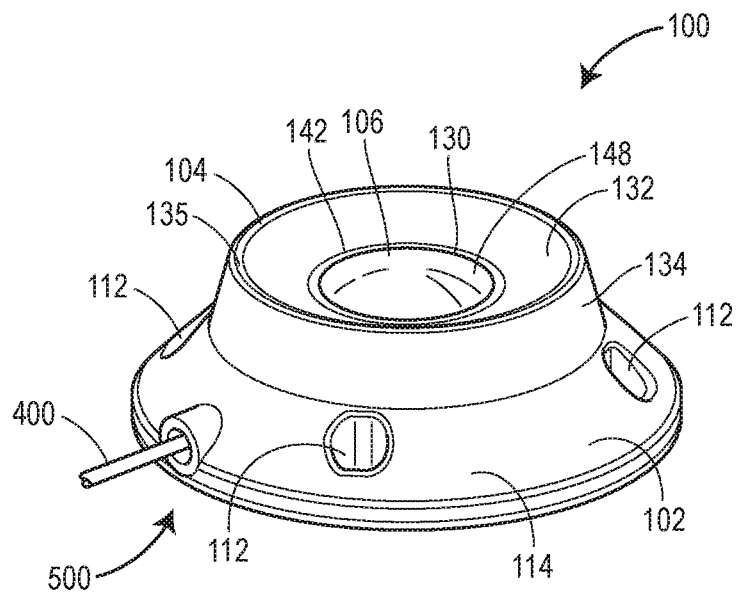
FIG. 1 is a perspective view of a first example port for a fluid delivery system in accordance with various embodiments.
Figure 2:
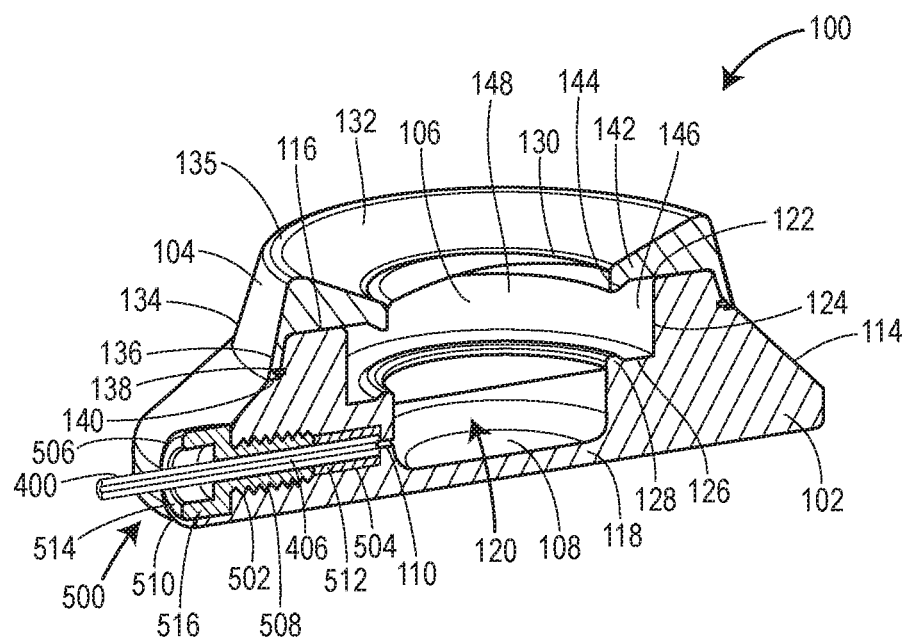
FIG. 2 is a cross-sectional view of the port of FIG. 1 showing an interior chamber and catheter connection assembly in accordance with various embodiments.
Figure 3:
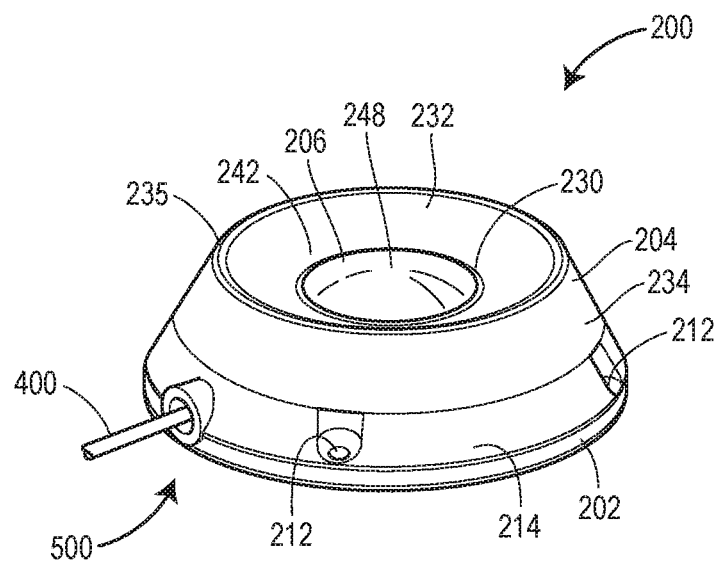
FIG. 3 is a perspective view of a second example port for a fluid delivery system in accordance with various embodiments.
Figure 4:
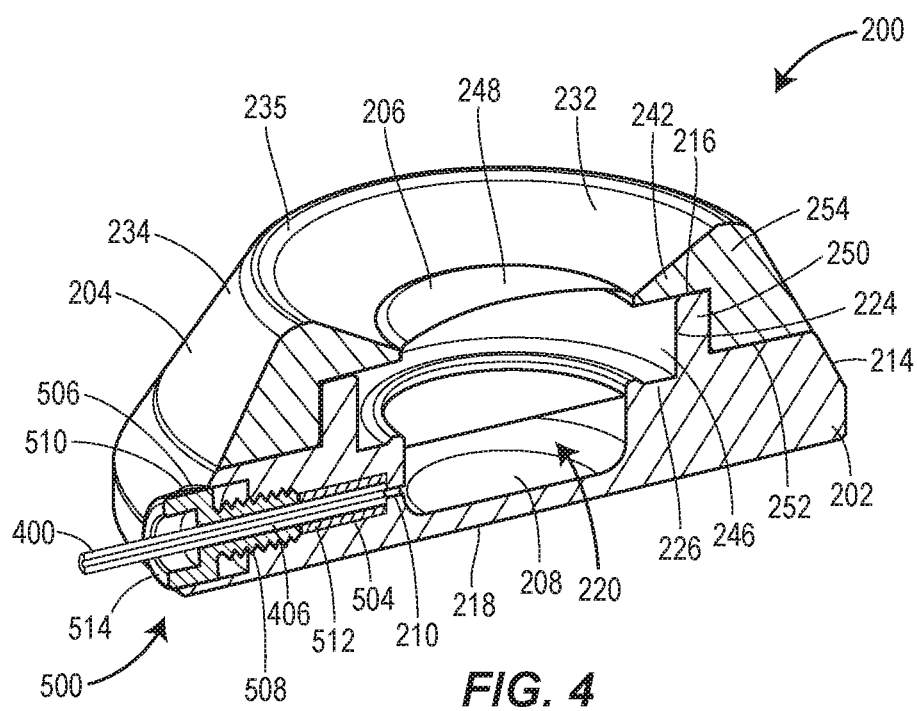
FIG. 4 is a cross-section view of the port of FIG. 3 showing an interior chamber and catheter connection assembly in accordance with various embodiments.

An example port 100 suitable for subcutaneous implantation is shown in FIGS. 1 and 2. The port 100 includes a body 102, a cap 104 coupled to the body 102, and a septum 106 providing needle access to a chamber 108 defined in the body 102. The chamber 108 includes a delivery opening 110 to dispense fluids to desired areas, described in more detail below. The port 100 can be anchored on a desired location within a patient selected by a clinician, such as a bony structure. For example, the body 102 can include one or more openings 112 extending therethrough to receive fasteners to mount the port 100 to the bony structure. Further, the openings 112 can be recessed with respect to adjacent portions of the body 102, so that head portions of the fasteners do not protrude beyond the body surface or only a portion thereof protrudes beyond the body surface. As shown, the port 100 can have a tapered profile with smooth exterior surfaces. This configuration advantageously mitigates skin erosion when the port 100 is implanted in a desired subcutaneous location.

As shown in FIG. 2, the body 102 has a frusto-conical shape with an outwardly tapering exterior surface 114 extending from an upper shoulder surface 116 to a bottom wall portion 118. The body 102 defines an interior cavity 120 having an opening 122 opposite the bottom wall portion 118. In the illustrated form, the body 102 extends around the interior cavity 120 in an annular configuration. The interior cavity 120 includes a lower portion defining the chamber 108 and an upper septum receiving portion 124. The chamber 108 can have smaller cross-sectional dimensions than the upper portion 124, such that a shoulder 126 extends between the upper portion 124 and the chamber 108 of the interior cavity 120. In the illustrated form, the upper portion 124 and the chamber 108 are cylindrical with the chamber 108 having a smaller diameter than the upper portion 124.

The upper portion 124 is sized to receive the septum 106 therein. For example, the septum 106 can have a disk shaped configuration and the diameter of the upper portion 124 can be approximately equal to, e.g., within 2 mm, to the diameter of the septum 106 so that the septum 106 is securely received within the upper portion 124. Further, as shown in FIG. 2, the shoulder 126 can include an upwardly projecting lip 128 that extends around an interior edge thereof and is configured to engage the septum 106.

In order to secure the septum 106 within the port 100, the cap 104 is coupled to the body 102 to trap the septum 106 therebetween. The cap 104 defines an interior opening 130 extending therethrough to provide needle access to the septum 106. In the illustrated form, the cap 104 is annular with a generally triangular cross-section in a longitudinal direction. So configured, the cap 104 includes an interior surface 132 that extends around and tapers downwardly toward the opening 130, an exterior surface 134 that tapers downwardly to the body 102, and a top edge 135. As shown, the cap 104 extends over an upper surface of the septum 106, with the cap 104 deforming the septum 106 and causing the upper surface of the septum 106 to protrude through the opening 130. With this configuration, the interior surface 132 can advantageously redirect a needle that has missed the septum 106 to the opening 130 and to the upper surface of the septum 106.

As shown, the cap 104 can further include a downwardly extending sidewall 136 that defines a portion of the exterior surface 134 and that projects along the body 102. In the illustrated form, the body 102 includes an outwardly opening groove 138 in the exterior surface 114 and the sidewall 136 of the cap 104 includes an inwardly projecting lip 140. So configured, the cap 104 can be press fit onto the body 102, deflecting the sidewall 136 until the lip 140 snap fits into the groove 138. With the cap 104 secured to the body 102, the cap 104 has an annular portion 142 extending over the cavity opening 122 and, in some versions, includes a downwardly projecting lip 144 extending therearound. So configured, an outer portion 146 of the septum 106 is trapped between the annular portion 142 of the cap 104 and the shoulder 126 of the body 102, while a central portion 148 of the septum 106 provides a clear path to the chamber 108. The lips 128, 144 project towards one another on opposite sides of the septum 106 to pinch the septum 106 therebetween to both secure the septum 106 and ensure a fluid tight seal. In some versions, the thickness and diameter of the septum 106 can be optimized to provide a low-profile port 100, while also providing a sufficiently large diameter for the central portion 148 so that the septum 106 can be easily located and identified through tissue. Alternatively, the cap 104 can also include an internal thread configured to engage an external thread of the body 102 to secure the cap 104 thereto. In another example, the cap 104 can be ultrasonically welded to the body 102.

Another example port 200 suitable for subcutaneous implantation is shown in FIGS. 3-6. The port 200 of this form includes many similar features to the above described port 100 and, as such, only the differences will be described herein with components having similar reference characters. For example, the port 200 of this form includes a body 202, a cap 204 coupled to the body 202, and a septum 206 providing needle access to a chamber 208 defined in the body 202. The chamber 208 includes a delivery opening 210 to dispense fluids to desired areas, described in more detail below. The port 200 can be anchored on a desired location within a patient selected by a clinician, such as a bony structure.

In this form, the cap 204 and body 202 couple together so that exterior surfaces 234, 214 thereof align giving the port 200 a substantially unbroken exterior with a frusto-conical shape. Further, as shown in FIG. 2, the body 202 includes an intermediate upstanding wall portion 250 disposed between a shoulder 226 of a body cavity 220 and an exterior shoulder 252. The cap 204 seats on the exterior shoulder 252 of the body 202 with an inwardly extending top portion 254 seating on an upper surface 216 of the wall 250 with an annular portion 242 engaging the septum 206 as described above.

Figure 5:
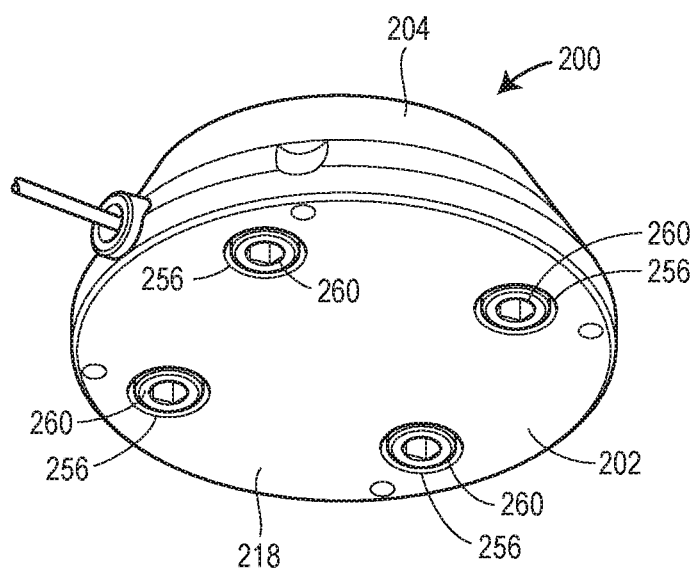
FIG. 5 is a bottom perspective view of the port of FIG. 3 in accordance with various embodiments.
Figure 6:
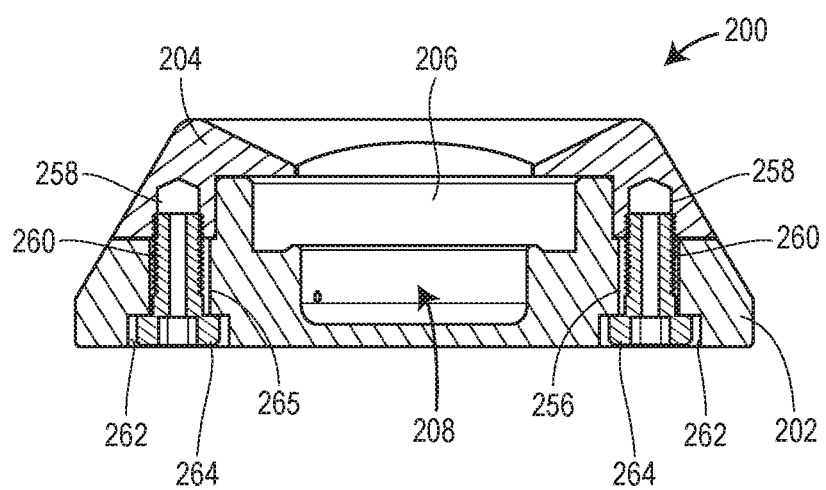
FIG. 6 is a cross-sectional vie of the port of FIG. 3 showing fastener connections between a body and cap of the port in accordance with various embodiments.

Another suitable method for securing the cap 204 to the body 202 is shown in FIGS. 5 and 6. In this form, the body 202 includes a plurality of throughbores 256 extending therethrough and the cap 204 includes corresponding bores 258 that align with the throughbores 256 of the body 202. So configured, fasteners 260 can be inserted through the bottom wall 218 of the body 202 and secured to the cap 204, such as by threading as shown. As the fasteners 260 tighten, the annular portion 242 of the cap 104 and the shoulder 126 of the body 202 traps the outer portion 246 of the septum 106 therebetween, while providing a clear path to the chamber 208 through the central portion 248 of the septum 206. If desired, the body 202 can include counterbores 262 in the bottom wall 218 thereof so that heads 264 of the fasteners 260 do not protrude beyond the bottom wall 218.

The components of the port 100, 200 can be formed from any suitable material. In some versions, one or more of the body 102, 202, cap 104, 204, septum 106, 206, or portions thereof, can be radiopaque for easy visualization under a fluoroscope or in an x-ray. In some examples, inner structures of the port 100, 200 can be polyether ether ketone (PEEK) or can have a PEEK layer on a metal housing, such as Titanium. Further, an outer shell, or needle facing surfaces can be metal, such as Titanium.

Figure 7:
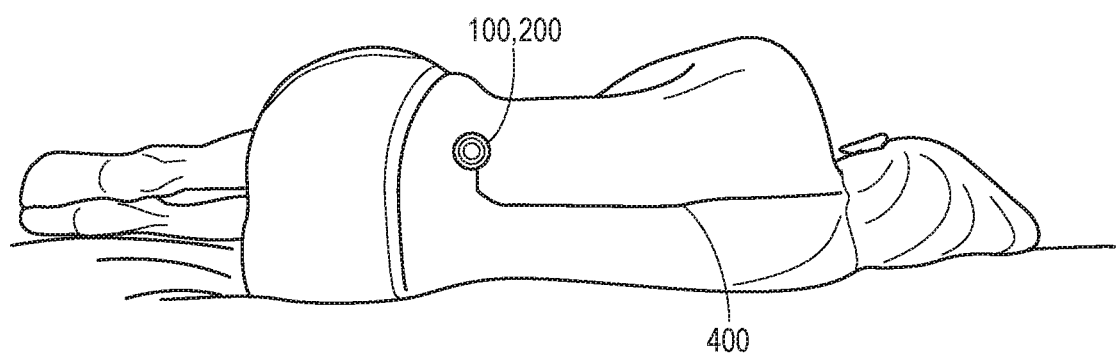
FIG. 7 is a schematic view of a fluid delivery system in accordance with various embodiments.
Figure 8:
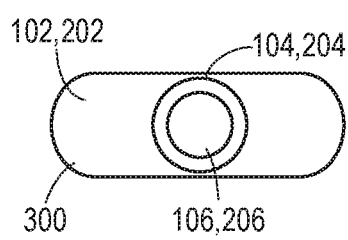
FIG. 8 is a top plan view of a port for a fluid delivery system having a first example body configuration for location feedback in accordance with various embodiments.
Figure 9:
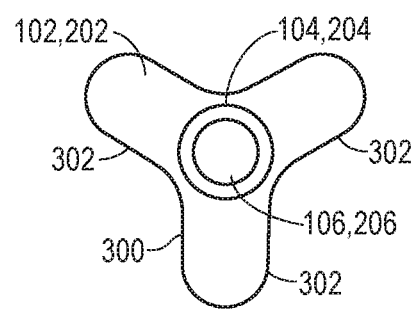
FIG. 9 is a top plan view of a port for a fluid delivery system having a second example body configuration for location feedback in accordance with various embodiments.
Figure 10:
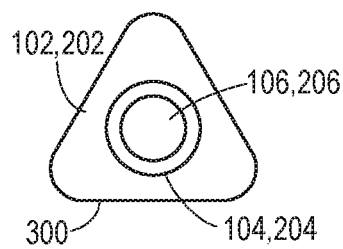
FIG. 10 is a top plan view of a port for a fluid delivery system having a third example body configuration for location feedback in accordance with various embodiments.
Figure 11:
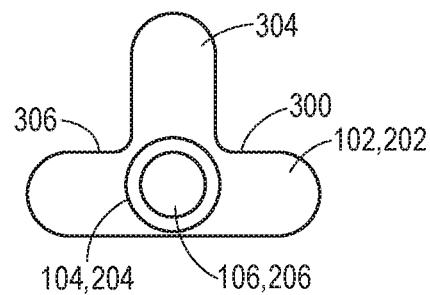
FIG. 11 is a top plan view of a port for a fluid delivery system having a fourth example body configuration for location feedback in accordance with various embodiments.

As discussed above, the port 100, 200 can include one or more features to aid in locating the port 100, 200 in a subcutaneous position. As shown in FIG. 7, a clinician can palpate and visually inspect the tissue of patient in order to locate the port 100, 200. In some forms, the body 102, 202 can include a housing 300 having a distinctive shape providing palpatory feedback to a clinician through the tissue of patient. For example, the housing 300 can have an oval or track-shaped cross-section as shown in FIG. 8, can have three or more outwardly extending branches 302 as shown in FIG. 9, can have a triangular cross-section as shown in FIG. 10, or can have an oval or track-shaped cross-section with a prong 304 extending outwardly from a side edge 306 thereof as shown in FIG. 11.

Figure 12:
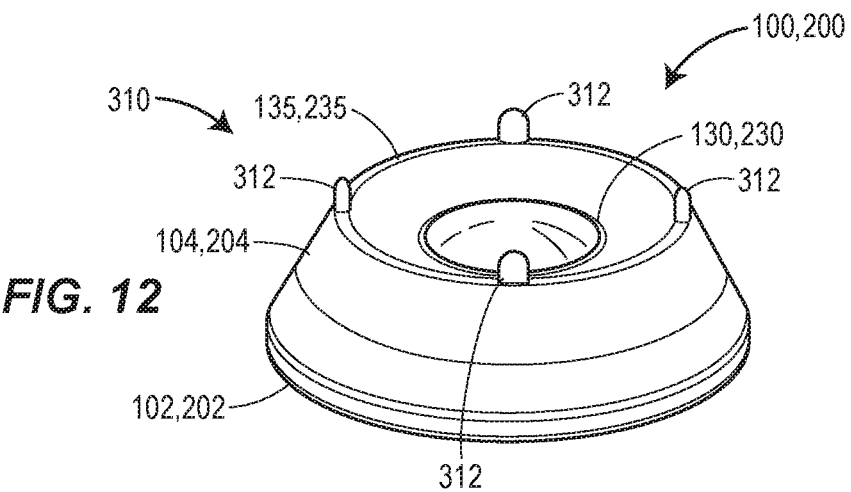
FIG. 12 is a perspective view of a first example port for a fluid delivery system having location feedback features in accordance with various embodiments.
Figure 13:
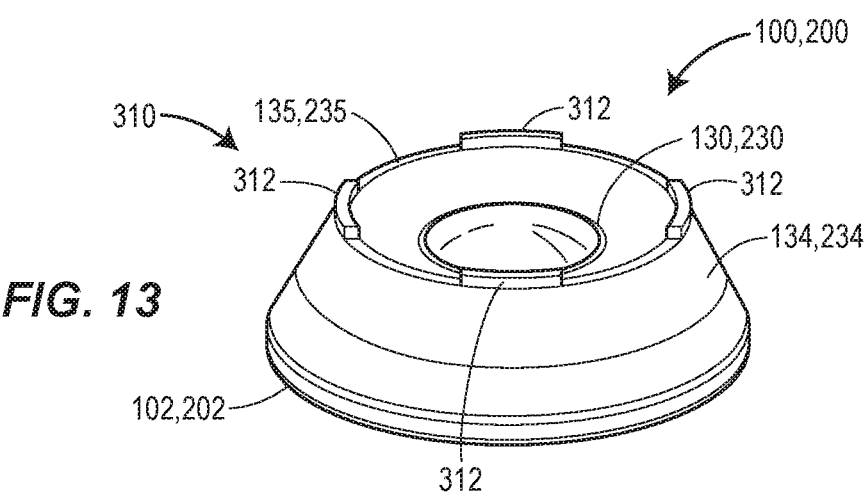
FIG. 13 is a perspective view of a second example port for a fluid delivery system having location feedback features in accordance with various embodiments.
Figure 14:
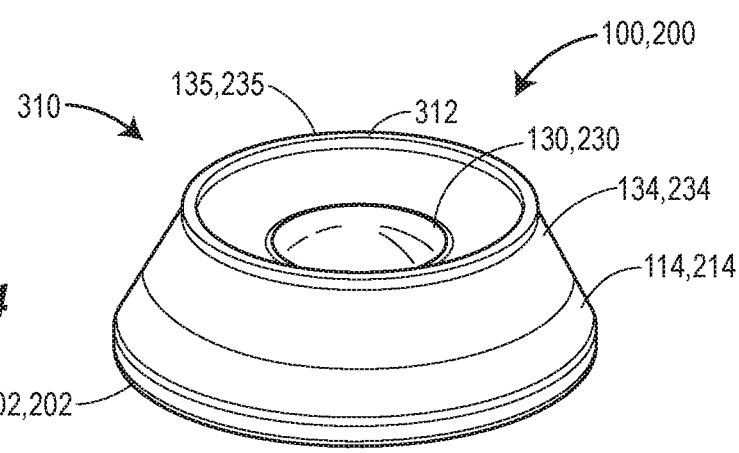
FIG. 14 is a perspective view of a third example port for a fluid delivery system having location feedback features in accordance with various embodiments.

In another example, the port 100, 200 can include protruding features 310 providing distinct palpatory feedback to a clinician through the tissue of a patient by virtue of differences in surface height as compared to adjacent portions of the cap 104, 204 and/or body 102, 202. In some examples, the cap 104, 204 can include a plurality of raised protrusions 312 extending above the top edge 135, 235 thereof and distributed around the opening 130, 230 as shown in FIGS. 12-14. The raised protrusions 312 can be disposed on the top edge 135, 235, the interior surface 132, 232, the exterior surface 134, 234, or combinations thereof. The raised protrusions 312 can take any suitable form, including rounded nodes as shown in FIG. 12, arcs as shown in FIG. 13, and a raised wall or lip as shown in FIG. 14. The features 310 can have a rounded or rectangular profile and can be provided in any suitable amount, such as four as shown in the figures, two, three, five, six, or more. Of course, while the protruding features 310 have been described with reference to the cap 104, 204, the body 102, 202 can also or alternatively include similarly configured protruding features 310.

Figure 15:
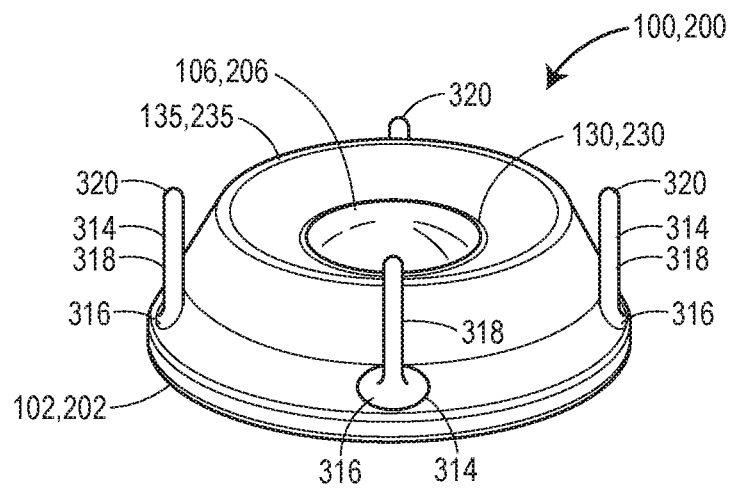
FIG. 15 is a perspective view of a fourth example port for a fluid delivery system having location feedback features in accordance with various embodiments.

In another example, the port 100, 200 can include upwardly protruding suture plugs 314, which can be filled with silicone, to provide palpatory feedback to a clinician through the tissue of patient. As shown in FIG. 15, a base 316 of the suture plugs 314 can be mounted to the body 102, 202 and distributed around the central septum 106, 206 with a shaft 318 extending upwardly from the base 316 having a distal end 320 disposed above the top edge 135, 235 of the cap 104, 204. The suture plugs 314 can have any suitable cross-section, such as circular or rectangular, and can be provided in any suitable amount, such as four as shown in the figures, two, three, five, six, or more. Of course, while the suture plugs 314 have been described with reference to the body 102, 202, the cap 104, 204 can also or alternatively include similarly configured suture plugs 314.

Figure 16:
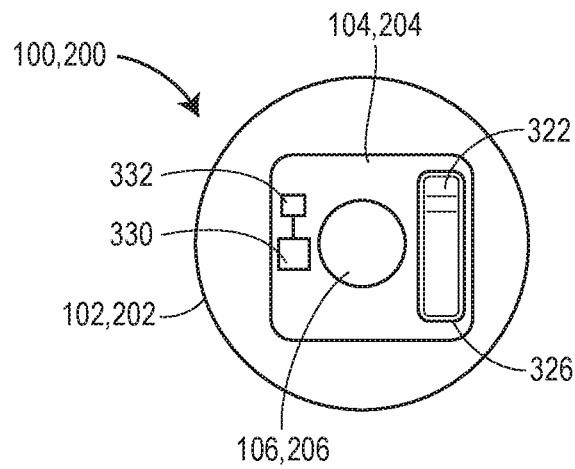
FIG. 16 is a top plan view of a fifth example port for a fluid delivery system having location feedback features in accordance with various embodiments.
Figure 17:
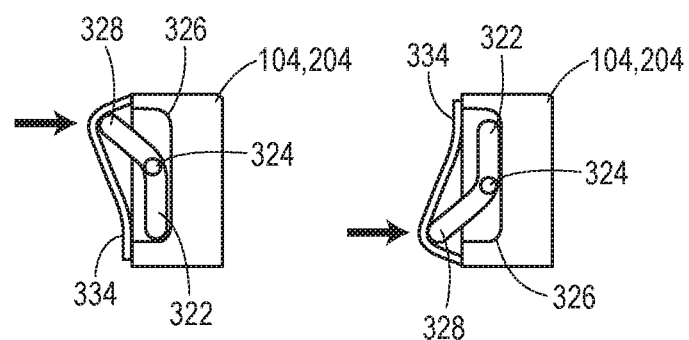
FIG. 17 is a side view of the port of FIG. 16 showing first and second states of a lever of the port in accordance with various embodiments.

In another example, as shown in FIGS. 16 and 17, the port 100, 200 can include a lever 322 pivotable about a pin 324. The lever 322 is disposed within a recess 326 within the cap 104, 204 or body 102, 202 and has an angled configuration, so that a portion 328 is always projecting out of the recess 326. With this configuration, a clinician can manipulate the lever 322 and the pivoting action of the lever 322 will provide tactile and visual feedback through the tissue. By another approach, the port 100, 200 can include a switch 330, such as a pushbutton or slide switch. Actuation of the switch 330 can provide tactile feedback to a clinician. Further, the switch 330 can be electrically coupled to an LED or other light source 332, such that actuation of the switch 330 energizes the LED 332 providing visual feedback to a clinician upon actuation. The lever 322, recess 326, switch 330, and/or LED 332 can be encapsulated or covered with a protective layer 334 adhered or otherwise secured to the port 100, 200 to prevent tissue from interfering with the feedback response and movement of the components.

In another example, as shown in FIGS. 18 and 19, the port 100, 200 can include a plurality of LEDs or other light sources 336 embedded into the body 102, 202 and/or cap 104, 204. The LEDs 336 can be electrically coupled together and to a first coil 338. So configured, a clinician can bring an external device 340 having a second coil 342 emitting an electromagnetic field into range of the first coil 338 to transfer energy and thereby energize the LEDs 336 providing visual feedback to the clinician. In a first form as shown in FIG. 18, the LEDs 336 can be disposed around the opening 130, 230 and directed inwardly to selectively illuminate the septum 106, 206. In a second form as shown in FIG. 19, the LEDs 336 can be disposed around the opening 130 and directed upwardly to selectively provide illumination through the tissue of the patient. Any number of LEDs 336 can be utilized, such as four or five as shown, two, three, six, or more.

In another example, as shown in FIG. 20, the port 100, 200 can include a plurality of piezoelectric crystals 344 embedded into the body 102, 202 and/or cap 104, 204. So configured, a clinician can bring an external device 346 emitting an electric field into range of the piezoelectric crystals 344 to cause the piezoelectric crystals 344 to vibrate and provide tactical and visual feedback to the clinician. If desired, as shown in FIG. 21, the piezoelectric crystals 344 can be distributed around the opening 130, 230 and sized to protrude from adjacent surfaces of the body 102, 202 and/or cap 104, 204 to provide tactile feedback similar to the above-described protruding features 310. For example, the piezoelectric crystals 344 can extend past the top edge 135, 235 of the cap 104, 204.

Figure 22:
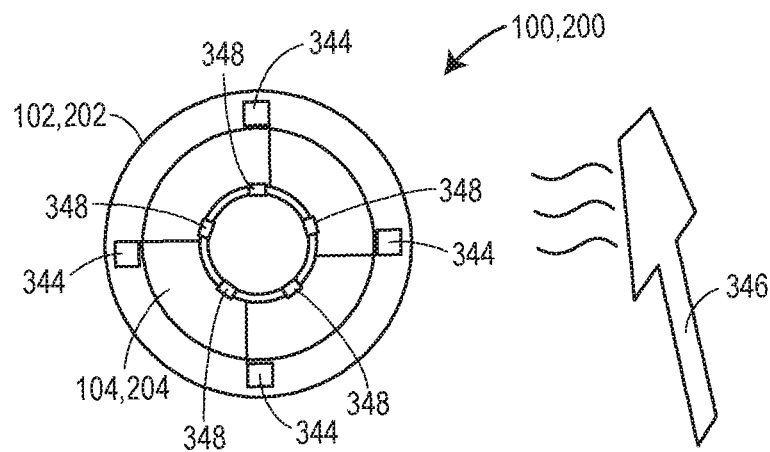
FIG. 22 is a top plan view of a ninth example port for a fluid delivery system having location feedback features in accordance with various embodiments.

Further, palpating the piezoelectric crystals 344 causes the piezoelectric crystals 344 to emit a voltage. Accordingly, as shown in FIG. 22, the port 100, 200 can include a plurality of LEDs or other light sources 348 embedded into the body 102, 202 and/or cap 104, 204. The LEDs 348 can be electrically coupled together and to the piezoelectric crystals 344. So configured, a clinician can find the piezoelectric crystals 344 through vibration and subsequently palpate the piezoelectric crystals 344 to emit a voltage and energize the LEDs 348. The LEDs 348 can be configured to illuminate the septum 106, 206 and/or outwardly as described above with respect to FIGS. 18 and 19.

Figure 23:
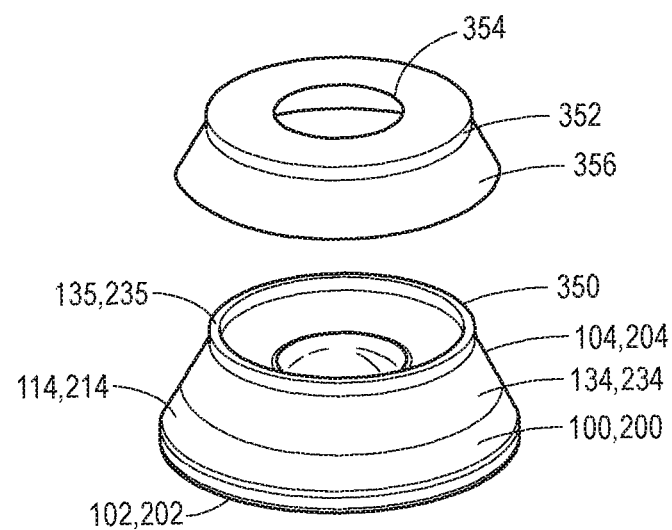
FIG. 23 is a perspective view of a tenth example port for a fluid delivery system having location feedback features with an external guide in accordance with various embodiments.

In another example, as shown in FIG. 23, the top edge 135, 235 of the cap 104, 204 can have a raised lip 350 and an external guide 352 can include a central opening 354 configured to mate with and around the raised lip 350. The external guide 352 can further include a skirt 356 depending downwardly from the central opening 354 so that a profile of the skirt 356 is complementary to external surfaces 114, 214, 134, 234 of the body 102, 202 and cap 104, 204. So configured, a clinician can locate the port 100, 200 and place the guide 352 onto the port 100, 200 through the tissue of the patient and the opening 354 and skirt 356 will orient the guide 352 to non-invasively identify the location of the septum 106, 206 through the opening 354.

Figure 24:
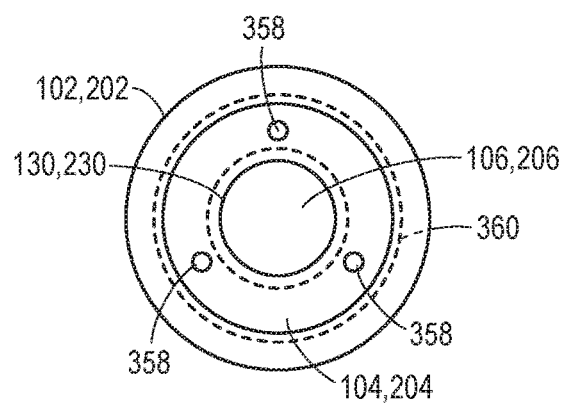
FIG. 24 is a top plan view of an eleventh example port for a fluid delivery system having location feedback features in accordance with various embodiments.
Figure 25:
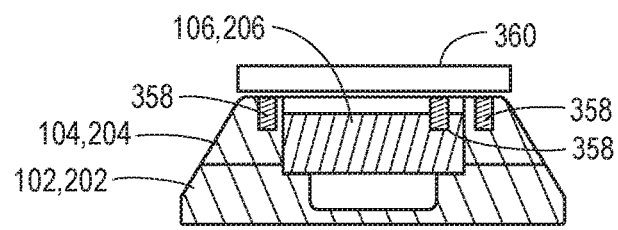
FIG. 25 is a side elevational view of the port of FIG. 24 with an external metallic guide in accordance with various embodiments.

In another example, as shown in FIGS. 24 and 25, the port 100, 200 can include a plurality of magnets 358 embedded into the body 102, 202 and/or cap 104, 204 and distributed around the opening 130, 230. So configured, a clinician can bring an external metallic ring 360 into range of the magnets 358 and the magnets 358 will attract the ring 360 to the port 100, 200 through the tissue of the patient. The magnets 358 orient the ring 360 to frame the opening 130, 230 on top of the tissue of the patient to provide an external indication of the location of the septum 106, 206. Any number of magnets 358 can be utilized, such as three as shown, two, four, five, six, or more, to optimize the strength and locationing of the guide 352.

Figure 26:
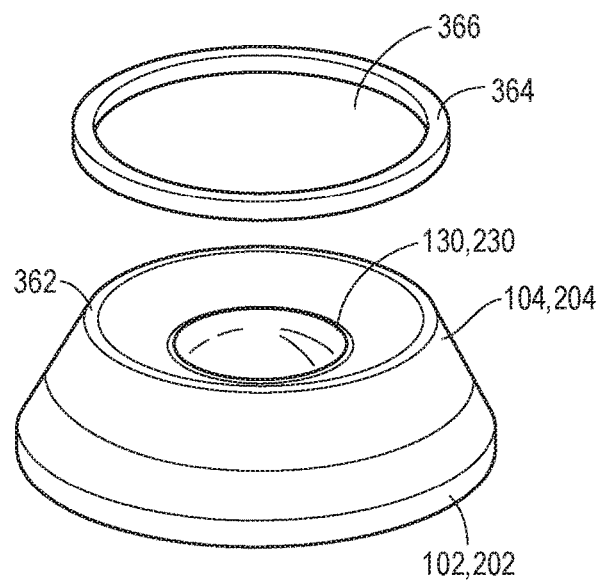
FIG. 26 is a perspective view of a twelfth example port for a fluid delivery system having location feedback features with an external magnetic guide in accordance with various embodiments.

In an alternative example, as shown in FIG. 26, the port 100, 200 can include a metallic ring 362 extending around the opening 130, 230 and mounted to or forming a portion of the body 102, 202, and/or cap 104, 204. Although an unbroken ring 362 is shown, it will be understood that the ring 362 can be formed from a plurality of spaced portions. With this configuration, a clinician can bring an external magnetic guide 364 having an interior opening 366 into range of the metallic ring 362 and the magnetic guide 364 will be attracted to the metallic ring 362 of the port 100, 200 through the tissue of the patient. The magnetic guide 364 is then oriented and held on the tissue of the patient so that the opening 366 frames the opening 130, 230 to provide an external indication of the location of the septum 106, 206. The magnetic guide 364 can be formed entirely of a magnetic material or can include a plurality of magnets mounted thereto. Any number of magnets can be utilized to optimize the strength and locationing of the guide 364.

Figure 27:
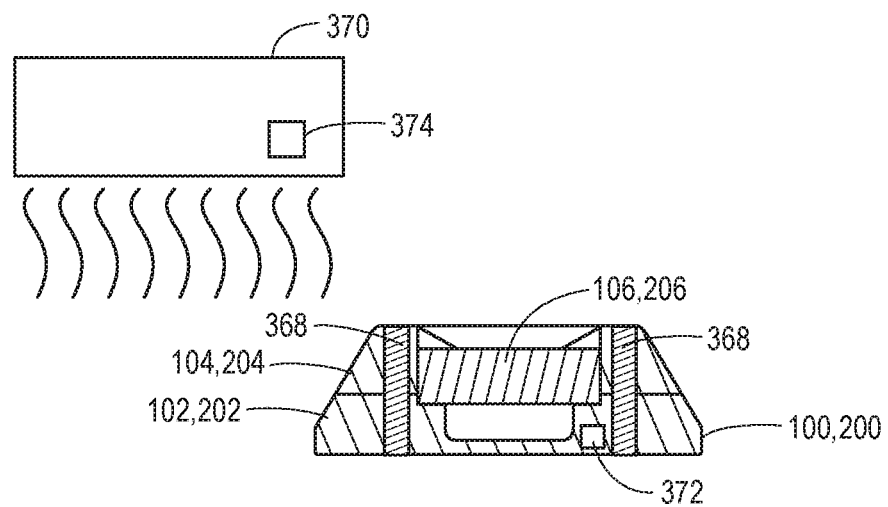
FIG. 27 is a side elevational view of a thirteenth example port for a fluid delivery system having location feedback features with an external metal detector in accordance with various embodiments.

In another example, as shown in FIG. 27, the port 100, 200 can include metallic portions or components 368 of a sufficient size to be detectable by an external metal detector 370. So configured, a clinician can operate the metal detector 370 and move the detector 370 along the patient's body until the detector 370 indicates the presence of the metallic components 368. Thereafter, the clinician can palpate the tissue to identify the location of the septum 106, 206. The metallic components 368 can be fasteners, layers, or portions of the body 102, 202 and/or cap 104, 204. In an alternative example, the port 100, 200 can include a transmitter 372 can be passive and energized by an external device 370 with a receiver 374, such as that described above with respect to FIGS. 18 and 19. So configured, the can operate the device 370 and move the device 370 along the patient's body until the device 370 energizes the transmitter 372 and receives a signal from the transmitter 372. Thereafter, the clinician can palpate the tissue to identify the location of the septum 106, 206.

Figure 28:
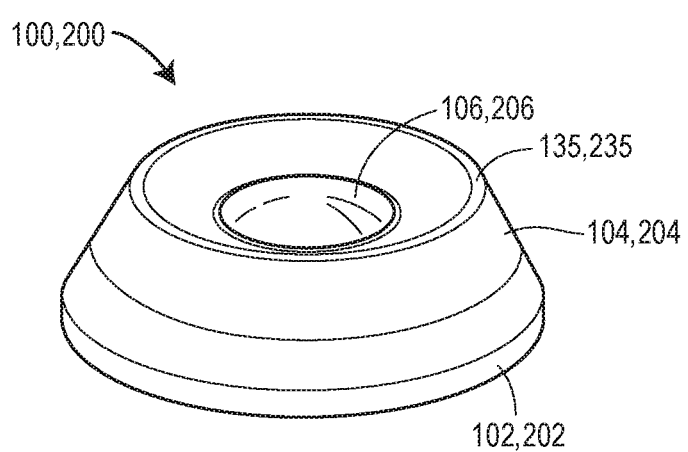
FIG. 28 is a perspective view of a fourteenth example port for a fluid delivery system having location feedback features in accordance with various embodiments.

In an alternative example, as shown in FIG. 28, the port 100, 200 can include a combination of metallic and non-metallic components to provide distinct appearance under imaging. For example, the port 100, 200 can include rings of metallic and non-metallic portions, the body 102, 202 can be metallic, the cap 104, 204 can be metallic, or combinations thereof. In further examples, the septum 106, 206 can be radiopaque so that a clinician can clearly distinguish between the various components and the location of the septum 106, 206 under imaging. Alternatively, the septum 106, 206 can be filled with aqueous gel materials that are detectable by an ultrasound machine.

Figure 29:
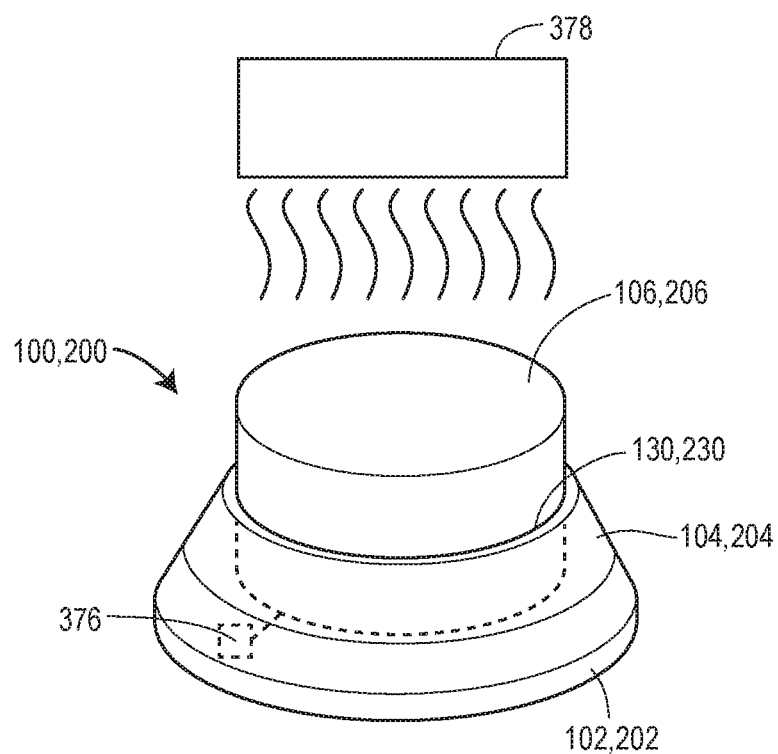
FIG. 29 is a perspective view of a fifteenth example port for a fluid delivery system having location feedback features with an external device in accordance with various embodiments.

In another example, as shown in FIG. 29, the port 100, 200 can be configured so that the septum 106, 206 can be raised through the central opening 130, 230. The septum 106, 206 can be raised by a lifting mechanism 376 disposed within the port 100, 200 and engaging the septum 106, 206. The lifting mechanism 376 can be any suitable device, including actuators, springs, motors, magnets, and so forth. The lifting mechanism 376 can be operable in response to communication or influence by an external tool 378. For example, the tool 378 can send a wireless command to the lifting mechanism 376 and/or can include metallic or magnetic components. The septum 106, 206 can be lifted to a raised position as shown to provide visible and tactile feedback to a clinician for locating the port 100, 200. Further, the raised septum 106, 206 can be utilized during infusion, described in more detail below.

Figure 30:
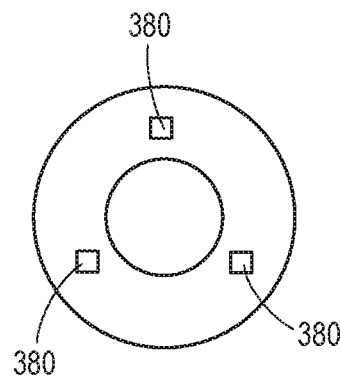
FIG. 30 is a top plan view of a sixteenth example port for a fluid delivery system having location feedback features in accordance with various embodiments.
Figure 31:
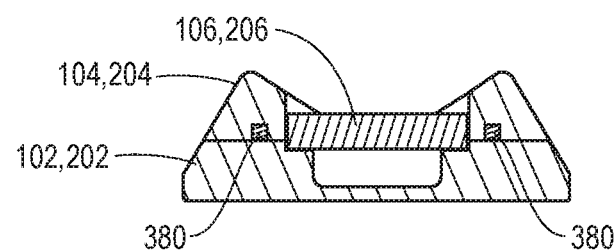
FIG. 31 is a side plan view of the port of FIG. 30 in accordance with various embodiments.
Figure 32:
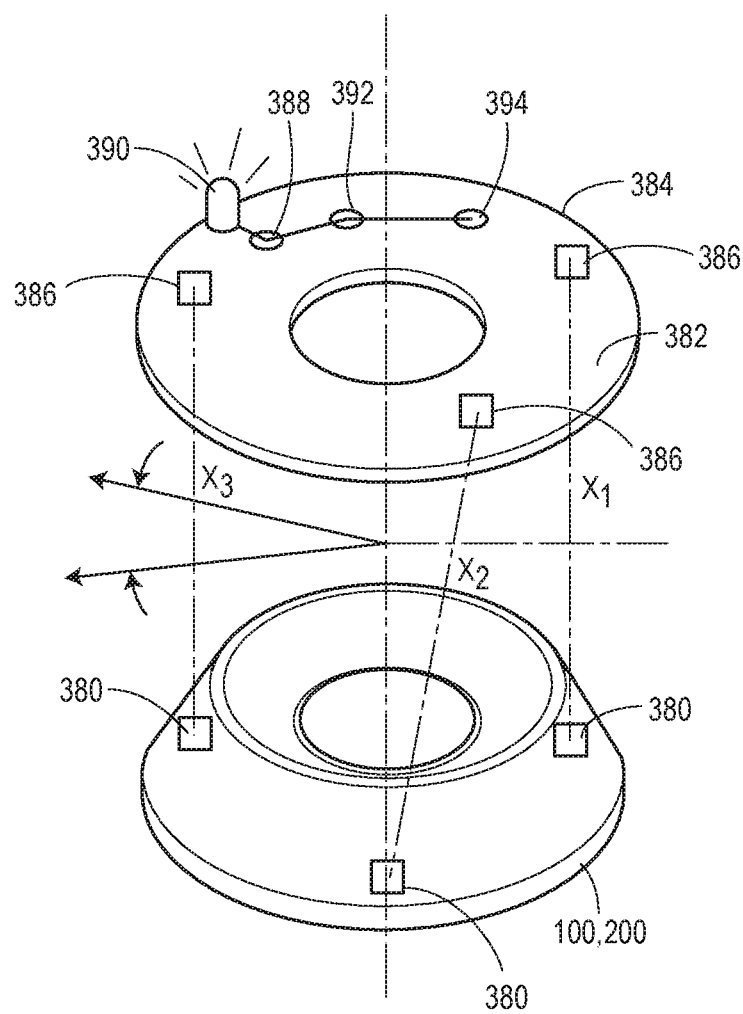
FIG. 32 is a perspective view of the port of FIG. 30 with an external device in accordance with various embodiments.

In another example, as shown in FIGS. 30-32, the port 100, 200 can include one or more sensors 380 embedded within the body 102, 202 and/or cap 104, 204 thereof. The sensors 380 can be passive and energized by an external device 382, such as that described above with respect to FIGS. 18 and 19. The external device 382 can include a housing 384 with corresponding sensors 386 and a processor 388. The sensors 380, 386 can be one or more of: proximity, infrared, pressure, ultrasonic, light, temperature, or tilt sensors. When energized, the sensors 380, 386 can provide data to the processor 388 of the external device 382 regarding the distance, axis alignment, orientation, relative angles, or combinations of the sensors 386 of the external device 382 relative to the sensors 380 of the port 100, 200. For example, the sensors 380, 386 can identify vertical alignment or misalignment therebetween, shown by vertical alignment X1 and angled alignment X2 in FIG. 32. Further, readings from the sensors 380, 386 can identify horizontal alignment, shown by the angle X3 in FIG. 32. The processor 388 can then analyze the data to calculate a position and/or orientation of the external device 382 relative to the port 100, 200 and provide feedback to a clinician. The external device 382 can provide feedback by any suitable mechanism, such as through lights 390, sounds through a speaker 392, a vibration device 394, or any other visual or tactile feedback to indicate that the external device 382 is properly aligned with the port 100, 200 for optimized needle insertion into and through the septum 106, 206. In further examples, the external device 382 can utilize multicolored lights 390 or other distinguishable feedback to communicate degrees of accuracy with different designated colors for alignment, such as red for misalignment, yellow for near alignment, and green for correct alignment.

Figure 33:
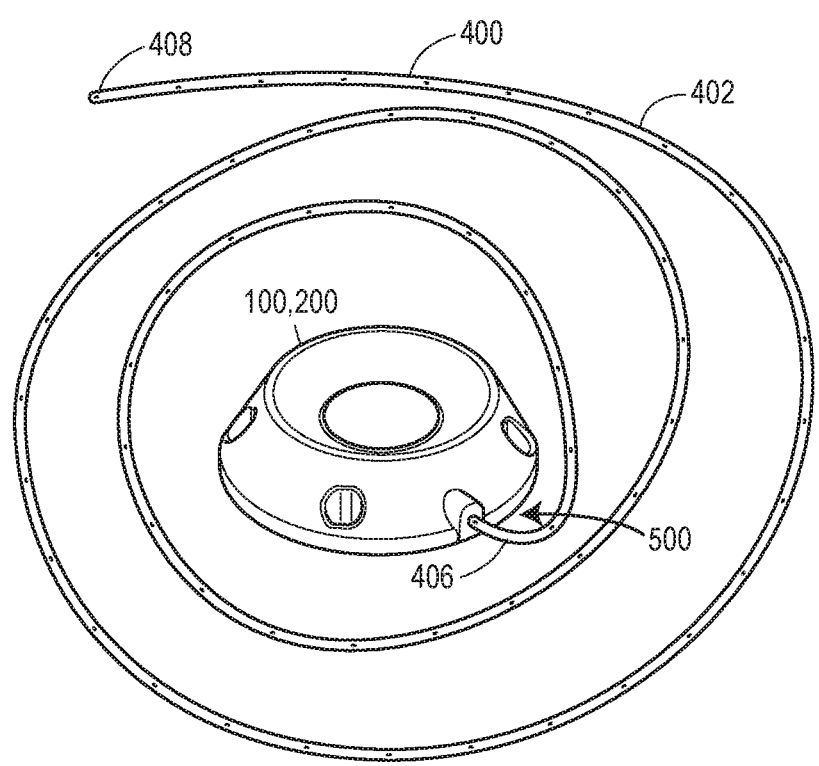
FIG. 33 is a top plan view of a fluid delivery system including a port and catheter in accordance with various embodiments.

Turning now to FIGS. 33-35, a catheter 400 can be coupled to the port 100, 200 to be fluidly coupled to the delivery opening 110 of the chamber 108 to dispense fluids to desired areas. The catheter 400 can be utilized to provide homogeneous delivery of composition (optionally comprising one or more therapeutic agents) to the intrathecal space of a patient. As such, the catheter 400 can be configured to extend along the substantially the entire length of a patient's spinal column or along any portion thereof. As shown, the catheter 400 includes an elongate, tubular body 402 having a central passage 404 extending from a proximal end 406 configured to couple to the port 100, 200 to a distal end 408.

Figure 34A:
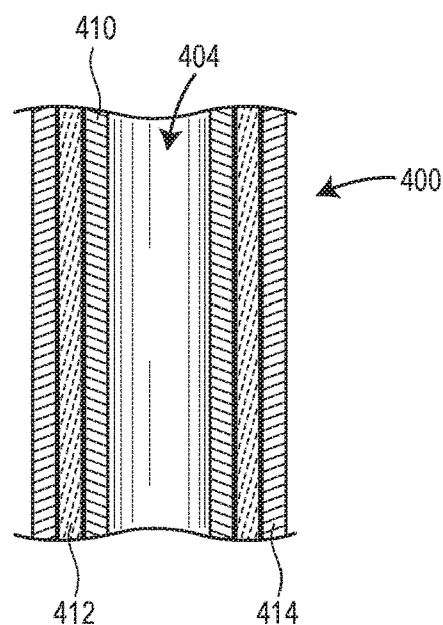
FIG. 34a is a cross-sectional view of a catheter having a first example construction in accordance with various embodiments.
Figure 34B:
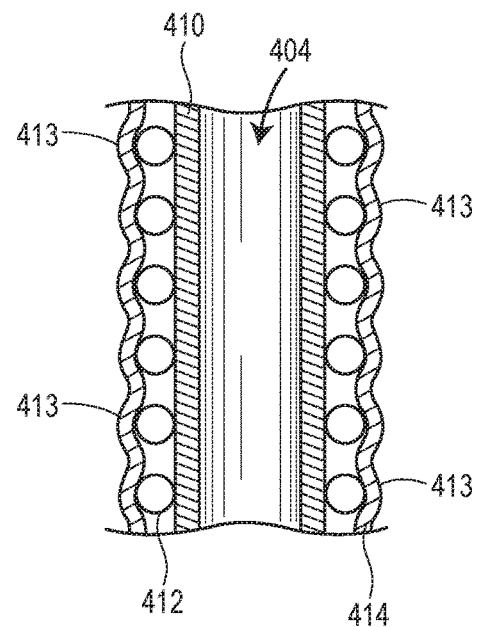
FIG. 34b is a cross-sectional view of a catheter having a second example construction in accordance with various embodiments.

The catheter 400 can be configured for long term implantation into a patient and, as such, can be constructed from materials to make the catheter soft, flexible, and kink resistant. Further, in some versions, the catheter 400 can be configured to complex spine patients, e.g., scoliosis, the materials can provide column strength, break resistance, and stiffness so that the catheter 400 can be threadable during insertion. Pursuant to this, some or all of the catheter 400 can have a three layer construction as shown in FIGS. 34a and 34b, including an inner lumen 410, a reinforcement layer 412, and an outer jacket 414. For example, the inner lumen 410 can be polytetrafluoroethylene (PTFE) or polyurethane (PU) and the outer jacket 414 can be an extrusion of PTSE, PU, or silicone and can include a hydrophilic coating. In some versions, the reinforcement layer 412 can be provided in the proximal end 406 to increase a hoop strength of the catheter 400 allowing a relatively higher compression without crushing damage, which may compromise the interior diameter of the catheter 400. This can advantageously be utilized to provide a strong connection and seal with the port 100, 200, several examples of which are described below. In a first example, as shown in FIG. 34a, the reinforcement layer 412 can be a suitable braided metal, such as stainless steel, or polymer, such as polyimide, polyethylene terephthalate (PET), and so forth. In a second example, as shown in FIG. 34b, the reinforcement layer 412 can be a series of rings or a coil causing the catheter to have outwardly extending radial protrusions 413. The radial protrusions 413 can be utilized in the connection with the port 100, 200, described in more detail below, subsidize the tensile strength of the connection.

Figure 36:
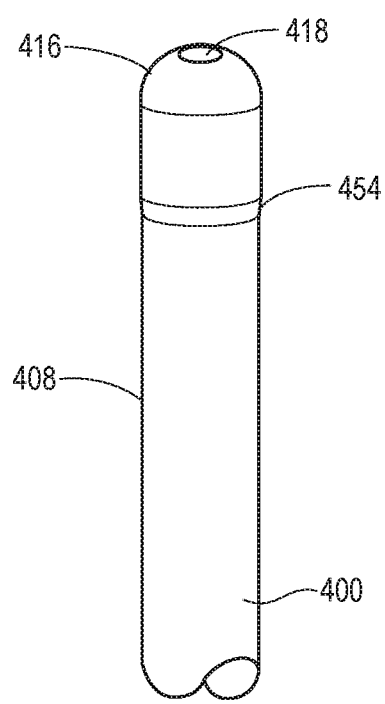
FIG. 36 is a sectional view of a distal end of the catheter of FIG. 34 in accordance with various embodiments.

As shown in FIG. 36, the distal end 408 of the catheter 400 can include an atraumatic tip 416 having a rounded profile and a distal outlet 418 extending therethrough to the central passage 404. The distal outlet 418 can be disposed along a longitudinal axis of the catheter 400 or can be disposed at an angle with respect thereto. The rounded profile of the atraumatic tip 416 allows the distal end 408 to be easily deflectable during insertion to avoid the end 408 from becoming lodged and aid in the catheter 400 being threaded through the intrathecal space. Further, the atraumatic tip 416 can allow implantation into the intrathecal space without damaging or exiting the intrathecal space.

Figure 37A:
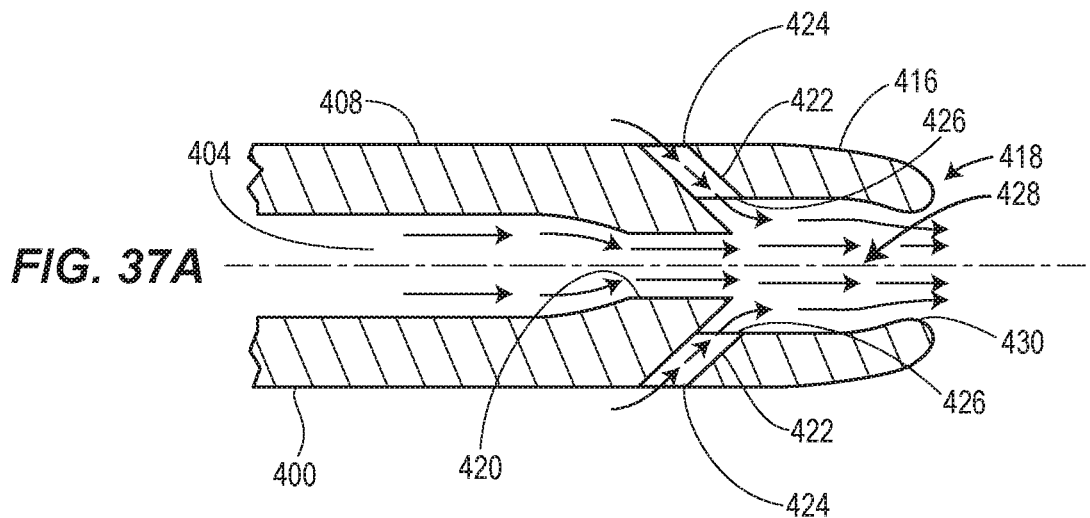
FIG. 37a is a cross-sectional view of a first example distal end for a catheter in accordance with various embodiments.

One example atraumatic tip 416 is shown in FIG. 37*a*. The tip 416 of this form includes a narrowing choke 420 connecting the central passage 404 to the distal outlet 418 where the choke 420 has a smaller diameter than the central passage 404 and distal outlet 418 creating a venturi effect, lowering fluid pressure and increasing fluid velocity through the tip 416. If desired, the distal outlet 418 can include a mixing chamber 428 having an inner diameter that is equal to or larger than the inner diameter of the central passage 404. Further, the distal outlet 418 can include a reduced-diameter opening 430 relative to the inner diameter of the mixing chamber 428. The opening 430 gives the distal outlet 418 a nozzle effect. Further, the tip 416 includes one or more side passages 422, such as two, three, four, or more, that extend from radial openings 424 to fluidly connect to the distal outlet 418. As shown, the side passages 422 can extend at an angle with respect to the longitudinal axis of the catheter 400 so that interior openings 426 of the side passages 422 are closer to the distal end 408 of the catheter 400 than the radial openings 424. With this configuration, the choke 420 creates a higher flow of therapeutic fluid through the catheter 400 with a lower pressure. Due to this, cerebrospinal fluid is drawn into the catheter 400 through the side passages 422 to join the flow of fluid creating a higher mass flow. Moreover, in the event that the distal outlet 418 becomes blocked or occluded, the side passages 422 can serve as secondary outlets for the catheter distal end 408.

Figure 37B:
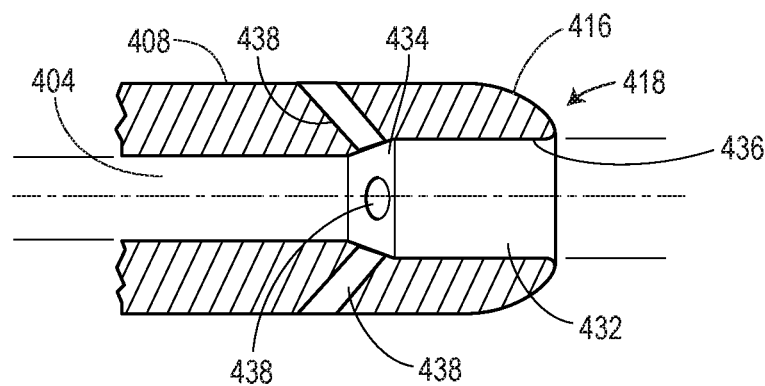
FIG. 37b is a cross-sectional view of a second example distal end for a catheter in accordance with various embodiments.

Another example atraumatic tip 416 is shown in FIG. 37*b*. In this form, the distal outlet 418 includes a mixing chamber 432 having an inner diameter larger than the inner diameter of the central passage 404 and a radially-tapering transition portion 434 extending between the central passage 404 and the mixing chamber 432. As shown, the distal outlet 418 can have a constant inner diameter extending from the mixing chamber to an outlet opening 436. The tip 416 can further include one or more side passages 438, such as two, three, four, or more, configured similar to the side passages 422 of the above form extending at an angle with respect to the longitudinal axis of the catheter. As shown, the side passages 438 can connect to the transition portion 434 to introduce cerebrospinal fluid to the flow of fluid through the catheter 400 providing flow mass amplification within the mixing chamber 432.

Figure 37C:
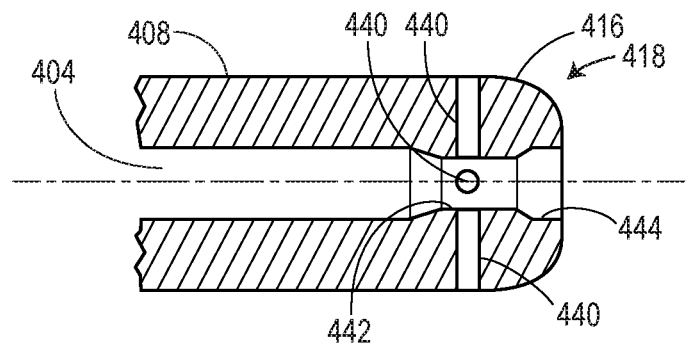
FIG. 37c is a cross-sectional view of a third example distal end for a catheter in accordance with various embodiments.

Another example atraumatic tip 416 is shown in FIG. 37*c* that includes side passages 440 and a narrowing choke 442. In this form, the side passages 440 extend radially through the catheter 400 and connect to the central passage 404 in the choke 442. Further, the inner diameter of the central passage 404 and an outlet opening 444 can be generally equal.

Figure 37D:
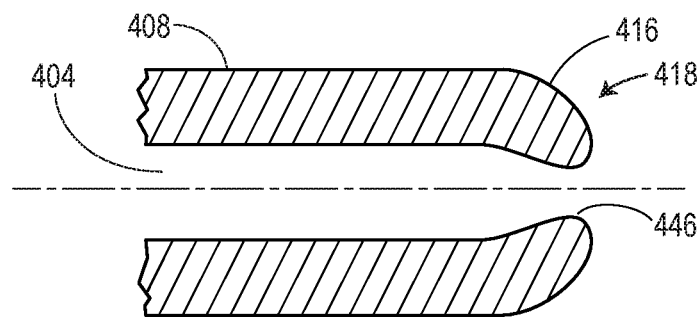
FIG. 37d is a cross-sectional view of a fourth example distal end for a catheter in accordance with various embodiments.

Another example atraumatic tip 416 is shown in FIG. 37*d*. In this form, the distal outlet 418 can include a reduced-diameter opening 446 relative to the inner diameter of the central passage 404. The opening 446 gives the distal outlet 418 a nozzle effect.

For some applications, it may be desirable to dispense a composition along a length of the catheter 400 into the intrathecal space of a patient. To achieve this, as shown in FIGS. 38*a*-38*d*, the catheter 400 can include one or more radial outlets 448 disposed along a length of the catheter 400 between the proximal and distal ends 406, 408 thereof. In a first example form, as shown in FIG. 38*a*, the radial outlets 448 can be disposed in a spiral configuration extending along a length and around a circumference of the catheter 400. The spiral configuration of this form ensures that the composition has a maximized exposure and spread within the intrathecal space.

In a second example form, as shown in FIG. 38*b*, the radial outlets 448 can be disposed in one or more rings 450 with the radial outlets 448 distributed about a circumference of the catheter 400. The rings 450 can be spaced from one another along the axial length of the catheter 400 and can be disposed within a plane generally normal to the axial length of the catheter 400. In a third example form, as shown in FIG. 38*c*, the radial outlets 448 can be disposed in one or more bands 452 running the axial length of the catheter 400. The catheter 400 can include one band 452 to distribute fluid in one radial direction, two, three, four, or more, as desired. In another example, as shown in FIG. 38*d*, the radial outlets 448 can include both one or more rings 450 and one or more bands 452.

In some versions, the distal and radial outlets 418, 448 can be sized to achieve a desired fluid distribution. In a first example, the distal and radial outlets 418, 448 can be sized so that a majority of fluid is dispensed through the distal outlet 418. In a second example, the distal and radial outlets 418, 448 can be sized so that an amount of fluid dispensed through the distal outlet 418 is generally equal to an amount of fluid dispensed through the radial outlets 448.

Figure 35A:
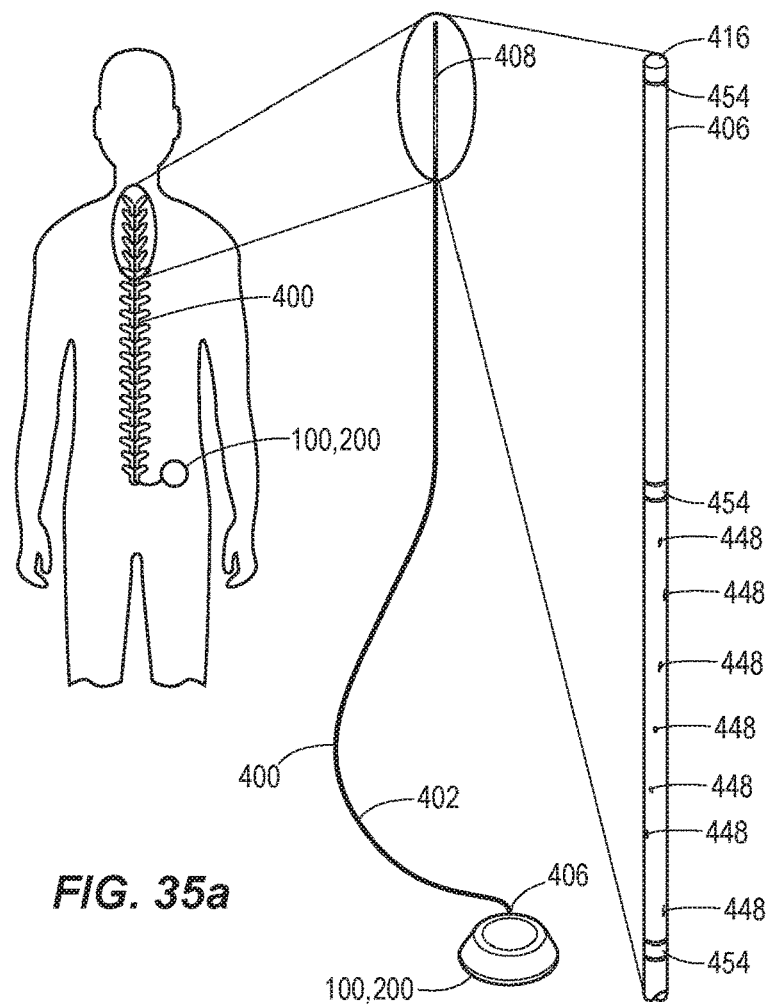
FIG. 35a is a schematic view of a fluid delivery system for implantation in the intrathecal space of a patient and portion of a catheter of the fluid delivery system in accordance with various embodiments.

In order to confirm that the catheter 400 has been correctly implanted into the intrathecal space and/or is in a fully functioning form, the catheter 400 may include one or more radiopaque markings or components to be visible under imaging. For example, the entire catheter 400 can be radiopaque or, as shown in FIG. 35*a*, the catheter 400 can include radiopaque markings 454 disposed at featured locations, such as below the distal end 406, adjacent to a start of the radial outlets 448, adjacent to an end of the radial outlets 448, and so forth.

In some examples, the catheter 400 can be provided with an extended length so that a clinician can cut the catheter 400 to a desired length for a particular patient. For example, the catheter 400 can be provided to the clinician with a length up to 140 cm. Further, the catheter 400 described herein can be a 3-fr, 1 mm outer diameter catheter. Other suitable outer diameters for the catheter 400 can be in the range of about 0.25 mm to about 1.5 mm, or in the range of about 0.5 mm to about 1.25 mm, or in the range of about 0.75 mm to about 1.0 mm.

Figure 35B:
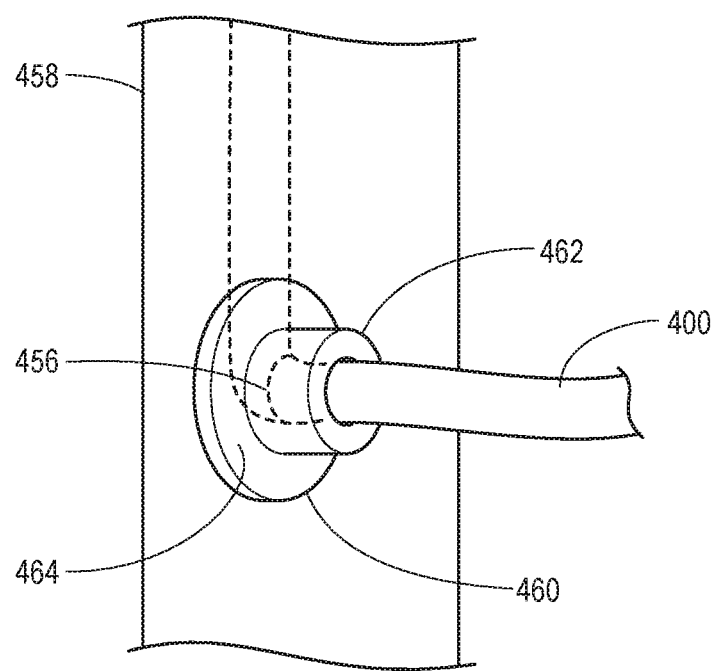
FIG. 35b is a schematic view of a catheter inserted into a dura of a patient with a grommet extending around the catheter and engaging the dura in accordance with various embodiments.

The spinal column of a patient is surrounded by a dura 458 that can be penetrated by a suitable instrument, such as a Tuohy needle, to create an opening 456 for the insertion of a catheter 400, configured as described above. As shown in FIG. 35*b*, in order to minimize or prevent tearing of the opening 456 and leakage of cerebrospinal fluid, a clinician can utilize a tissue engagement portion, which in this form is a grommet 460, to abut the dura 458 and extend around the opening 456 therein. The grommet 460 can include a sleeve portion 462 sized to extend around the catheter 400 and a flange portion 464 projecting outwardly from the sleeve portion 462 and configured to be placed on the dura 458 over and around the opening 456.

In some versions, the catheter 400 can further be provided or implanted along with a tissue engagement portion, which in this form is a plug 466 having a body 468 with a passage 470 extending therethrough for reception of the catheter 400. The passage 470 extends through the plug body 468 from a distal end 472 to an opposite, proximal end 474 thereof. As shown, one or both of the ends 472, 474 can have a beveled, frusto-conical configuration. Further, the body 468 can have a bent configuration with the distal end 472 at an angle with respect to the proximal end 474. For example, the body 468 can include a bend 476, that can be generally 90 degrees, e.g., within 5 to 10 degrees, as shown, although other acute or obtuse angles can also be utilized. In order to thread the catheter 400 through the plug 466, the body 468 can include an opening 478 that extends through the body 468 from the passage 470 to an exterior 480 of the plug 466. A clinician can utilize the opening 478 to manipulate the catheter 400 through the plug body 468 and out through the distal end 472.

A fascia 482 extends around the dura 458 and, as such, the fascia 482 can also be penetrated by the instrument to create an opening 484 therein in addition to the opening 456 in the dura 458. The plug 466 can advantageously be implanted through the opening 484 in the fascia 482 to create a seal with the tissue of the fascia 482 to minimize or prevent leakage of cerebrospinal fluid. The beveled configuration of the distal end 472 can also aid a clinician in inserting the plug 466 through the fascia 482.

Figure 35C:
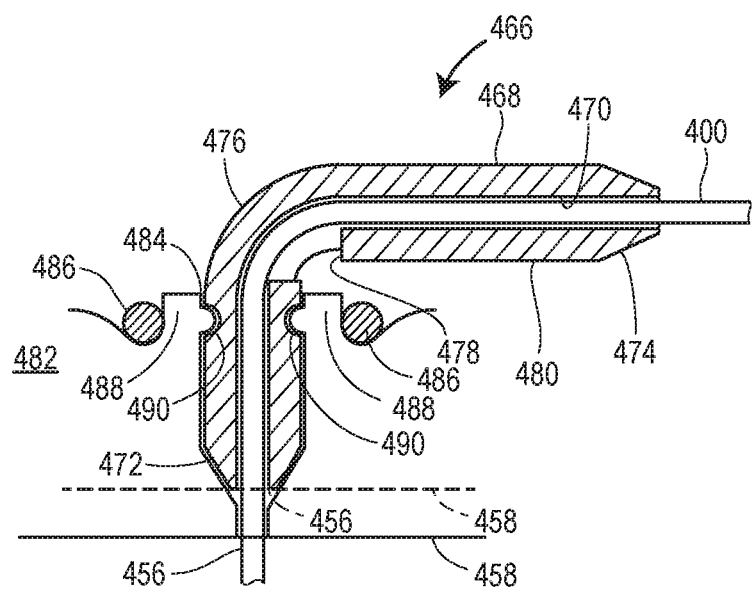
FIG. 35c is a cross-sectional view of a plug for a catheter inserted into the fascia in accordance with various embodiments.
Figure 35D:
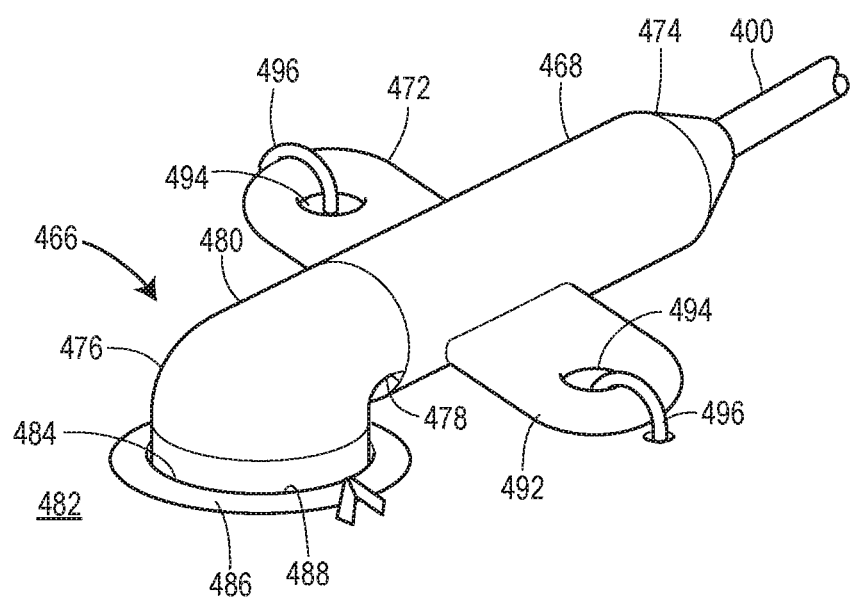
FIG. 35d is a perspective view of the plug of FIG. 35c in accordance with various embodiments.

In one approach, shown in broken lines in FIG. 35c, the plug 466 can be inserted into the fascia 482 until the distal end 472 abuts the dura 458. So configured, the distal end 472 can extend around the opening 456 to minimize or prevent tearing and cerebrospinal fluid leakage. In another approach, shown in solid lines in FIG. 35c, the plug 466 can be inserted into the fascia 482 with the distal end 472 spaced from the dura 458. In either approach, after the plug 466 is positioned, a clinician can stitch up the opening 484 in the fascia 482 with a suture 486 so that some tissue 488 of the suture 486 is captured between the suture 486 and the plug body 468. Thereafter, when the clinician tightens the suture 486, the tissue 488 is tightly captured between the suture 486 and the plug body 468 creating a seal preventing or minimizing the leakage of cerebrospinal fluid through the fascia opening 484. In some versions, the plug body 468 can include an annular recess 490 extending therearound, or a plurality of recesses distributed around the circumference, adjacent to the distal end 472. When the suture 486 is tightened, the tissue 488 can be drawn into the recess 488 preventing or minimizing subsequent movement of the suture 486.

As shown, the body 468 can further include outwardly projecting tabs 492 having openings 494 extending therethough. A clinician can utilize the tabs 492 to secure the proximal end 474 of the plug body 468 to the fascia 482 with sutures 492. Advantageously, the bent configuration of the body 468 allows the plug proximal end 474 to extend along the fascia 482 for a compact configuration after implantation. In one form, the plug 466 can be made of silicone or other suitable material.

In an alternative or additional approach, the catheter 400 can include a tissue engagement portion, which in this form is a portion of the catheter with an outwardly tapered configuration where the increased outer diameter is configured to engage the opening 456 in the dura 458 to minimize or prevent tearing.

As briefly described above, the catheter 400 can be configured to couple to the port 100, 200 to be fluidly coupled to the delivery opening 110, 210 of the chamber 108, 208. This can be achieved in a number of suitable connection assemblies 500, some or all of which can advantageously be free of metal components. In a first example, shown in FIGS. 2 and 4, the port 100, 200 can include a cylindrical cavity 502 extending radially through the body 102, 202 with the delivery opening 110, 210 at an interior end 504 and an open exterior end 506. The cylindrical cavity 502 can include a threaded portion 508 and a counterbore 510 at the open exterior end 506. Next, an annular gasket 512 can be placed over the proximal end 406 of the catheter 400 and the assembled gasket 512 and catheter 400 is inserted into the cavity 502 until the gasket 512 and catheter 400 abut the interior end 504 thereof. As shown, this aligns the central passage 404 of the catheter 400 with the delivery opening 110, 210. To secure the catheter 400 to the port 100, 200 and create a fluid tight seal, a ferrule 514 extending around the catheter 400 can be inserted into the cavity 502 to engage the threaded portion 508. As the ferrule 514 is threaded into the cavity 502, the ferrule 514 engages the gasket 512 and causes the gasket 512 to compress and radially expand to tightly engage the surface of the cavity 502 and the catheter 400. The counterbore 510 can be sized to receive a portion of a head 516 of the ferrule 514 to minimize outwardly protruding features on the port 100, 200. The gasket 512 can be a singular component or can be composed of multiple components, as desired.

For ease of installation, the inner diameter of the gasket 512 can be larger than an outer diameter of the catheter 400. Further, the proximal end 406 of the catheter 400 can be reinforced to have a higher hoop strength to withstand the compressive force generated by the gasket 512. If desired, the ferrule 514 and/or cavity 502 can include a torque limiting tool to prevent overtightening and the possible resulting damage to the catheter 400.

Figure 39:
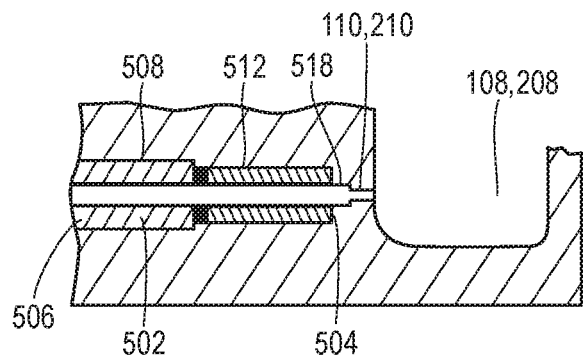
FIG. 39 is a cross-sectional view of a first example catheter and port connection assembly in accordance with various embodiments.

In an alternative example, as shown in FIG. 39, the cavity 502 can include a catheter counterbore 518 at the interior end 504 thereof. The catheter counterbore 518 has a diameter sized to receive a portion of the proximal end 406 of the catheter 400 therein, but also sized to be smaller than the gasket 512. With this configuration, the end of the catheter 400 is not compressed by the gasket 512 during tightening and therefore possible crushing of the end is prevented.

Figure 40:
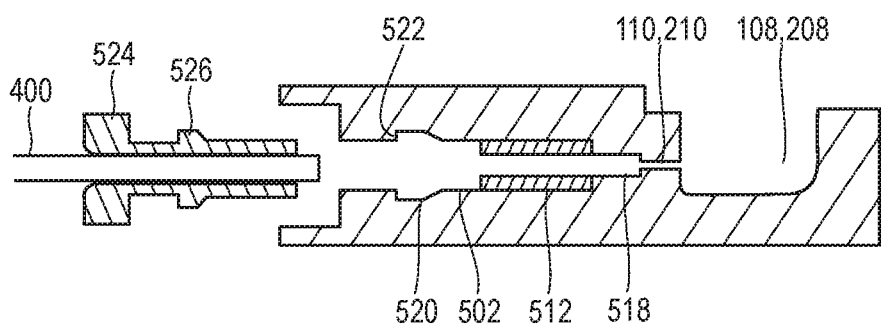
FIG. 40 is a cross-sectional view of a second example catheter and port connection assembly in accordance with various embodiments.

In another example, as shown in FIG. 40, the assembly 500 can utilize a snap-fit connection rather than a threaded connection as described above with respect to FIGS. 2, 4, and 39. Pursuant to this, the cavity 502 can include an annular snap-fit recess 520 having a radially outward stop surface 522 and a ferrule 524 can include an outwardly projecting annular prong 526. So configured, the ferrule 524, extending around the catheter 400, can be inserted into the cavity 502 until the prong 526 is biased into the recess 520 by the resiliency of the ferrule 524 and/or the catheter 400. The prong 526 engages the stop surface 522 of the recess 520, preventing removal of the ferrule 524. Further, the recess 520 can be located within the cavity 502 and the gasket 512 can be sized to provide an optimal amount of compression to result in a fluid tight seal without overly compressing the catheter 400. Although the recess 520 and prong 526 are described as annular, discrete portions that can be aligned during insertion is within the scope of this disclosure.

Figure 41:
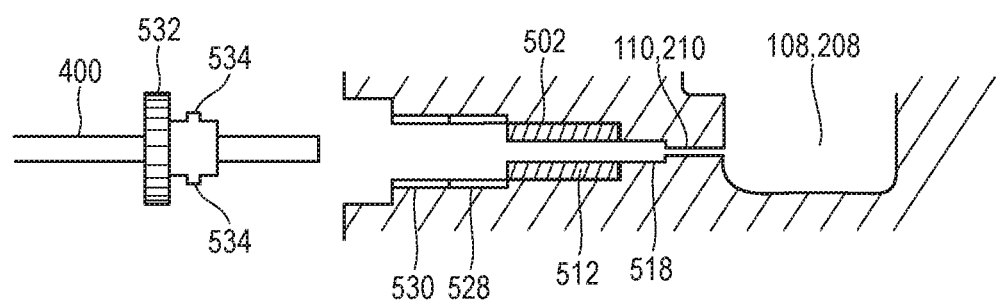
FIG. 41 is a cross-sectional view of a third example catheter and port connection assembly in accordance with various embodiments.

In another example as shown in FIG. 41, the assembly 500 can utilize a luer lock connection rather than a threaded or snap-fit connection as described above. Pursuant to this, the cavity 502 can include a plurality of radial recesses 528 with outwardly extending openings 530. A ferrule 532 of this form can include a plurality of radial tabs 534 that are positioned to align with the openings 530. For example, the tabs 534 and openings 530 can be symmetrically disposed around the ferrule 532 and cavity 502 respectively. During assembly, a clinician can align the tabs 534 with the openings 530, insert the ferrule 532 into the cavity 502 until the tabs 534 align with the radial recesses 528, and turn the ferrule 532 a predetermined amount, such as a quarter turn, to lock the ferrule 532 to the port 100, 200. By one approach, the radial recesses 528 can be sized to frictionally engage the tabs 534. Further, the radial recesses 528 can be located within the cavity 502 and the gasket 512 can be sized to provide an optimal amount of compression to result in a fluid tight seal without overly compressing the catheter 400.

Figure 42:
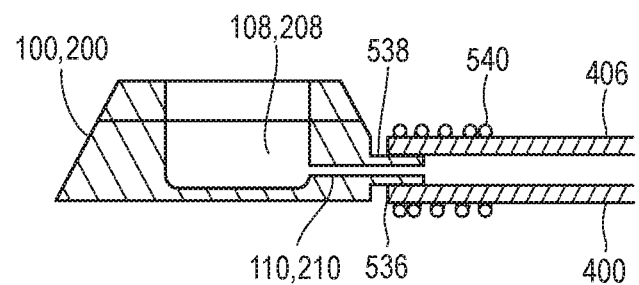
FIG. 42 is a cross-sectional view of a fourth example catheter and port connection assembly in accordance with various embodiments.

In another example, as shown in FIG. 42, the port 100, 200 can include an outwardly projecting tube 536 having a passage 538 extending from the delivery opening 110, 210 of the chamber 108, 208. In a first form, the tube 536 can have an outer diameter that is equal to or smaller than an inner diameter of the catheter proximal end 406 so that the proximal end 406 can be inserted over and around the tube 536. To secure the catheter 400 to the tube 536, a spring 540, which can be made of metal, such as nitinol, for example, having a resting state compressing the catheter 400, can be twisted to loosen the spring 540 to allow the catheter proximal end 406 to be inserted onto the tube 536 and released to compress and secure the catheter 400 to the port 100, 200. If desired, a clinician can utilize a tool to engage the spring 540 to easily loosen the windings thereof during assembly.

Figure 43:
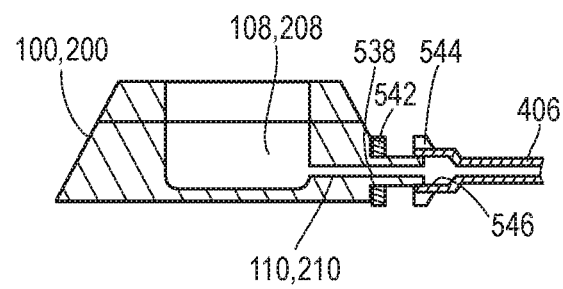
FIG. 43 is a cross-sectional view of a fifth example catheter and port connection assembly in accordance with various embodiments.

In another example, as shown in FIG. 43, the outwardly projecting tube 536 can include a backstop 542 extending around an intermediate portion thereof and the catheter proximal end 406 can have a press-fit ring 544 mounted thereto. As shown, the catheter proximal end 406 can have an expanded diameter to secure within the ring 544 and an interior opening 546 of the ring 544 can be sized to have a press-fit engagement with the tube 536. So configured, a clinician can simply align the opening 546 with the tube 536 and press the ring 544 until the ring 544 abuts the backstop 542.

Figure 44:
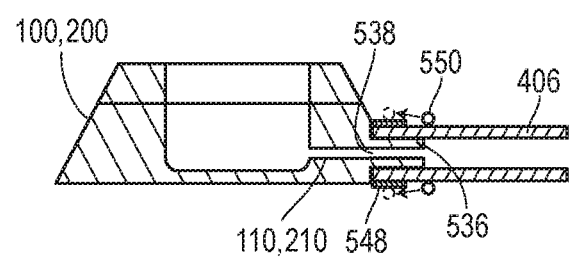
FIG. 44 is a cross-sectional view of a sixth example catheter and port connection assembly in accordance with various embodiments.

In another example, as shown in FIG. 44, the port 100, 200 can include an annular wall 548 encircling the tube 536. The assembly 500 of this form, can further include an o-ring 550 having an inner diameter smaller than an outer diameter of the catheter proximal end 406 such that the o-ring 550 provides a compressive force on the catheter 400 when mounted therearound. During assembly, the o-ring 550 can be shifted longitudinally along the catheter 400 so that the proximal end 406 can be fully inserted between the tube 536 and wall 548. Thereafter, the o-ring 550 can be stretched or rolled onto the wall 548 to provide a compressive force through the wall 548 to the catheter 400 and tube 536. By one approach, the inner diameter of the wall 548 can be generally equal, within 1 mm, of an outer diameter of the catheter 400 so that the catheter 400 is tightly received in the annular space between the wall 548 and tube 536. The o-ring 550 can be formed from rubber or any suitable elastomer, for example.

Figure 45:
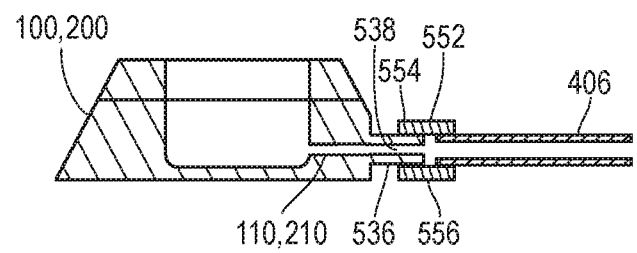
FIG. 45 is a cross-sectional view of a seventh example catheter and port connection assembly in accordance with various embodiments.

In another example, as shown in FIG. 45, the assembly 500 of this form can utilize a clamping member 552 to secure the catheter proximal end 406 to the tube 536. The clamping member 552 can include upper and lower portions 554, 556 that are movable with respect to one another to be clamped around the catheter proximal end 406 and the tube 536 during assembly. As shown, the catheter proximal end 406 and the tube 536 can be axially aligned in a lap joint connection so that the ends thereof abut one another and the clamping member 552 can be secured thereover to provide a fluid tight seal. The upper and lower portions 554, 556 can be secured together by any suitable mechanism, including snap-fit, crimping, an attachment member, and so forth.

Figure 46:
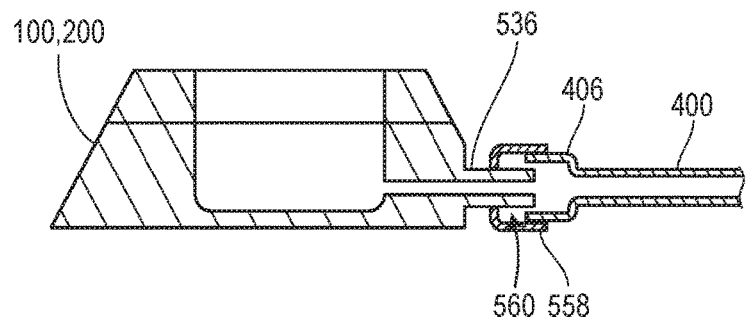
FIG. 46 is a cross-sectional view of an eighth example catheter and port connection assembly in accordance with various embodiments.

In another example, as shown in FIG. 46, the port 100, 200 can include an annular wall 558 encircling the tube 536 creating an annular catheter reception space 560 between the wall 558 and tube 536. The catheter proximal end 406 of this form can have an enlarged outer diameter as compared to the main body of the catheter 400, such that the proximal end 406 has greater hoop strength and can withstand greater compressive forces during assembly. Pursuant to this, the reception space 560 can be sized to receive the catheter proximal end 406 therein in a compressive, press-fit configuration to secure the catheter 400 to the port 100, 200 and form a fluid tight seal between the tube 536 and catheter 400.

Figure 47:
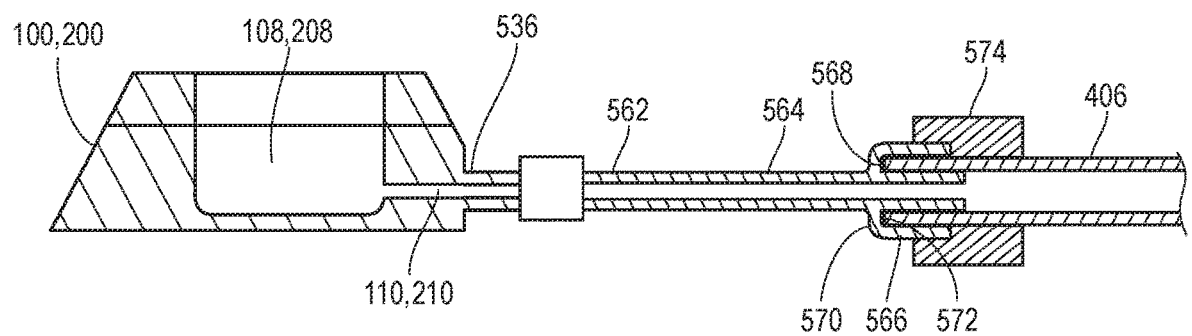
FIG. 47 is a cross-sectional view of a ninth example catheter and port connection assembly in accordance with various embodiments.

In another example, as shown in FIG. 47, the port 100, 200 can include a pre-connected assembly 562 including a flexible tube 564 secured to the body 102, 202 and fluidly connected to the delivery opening 110, 210 and a connector 566. The connector 566 includes a central stem 568 and surrounding housing 570 that define an annular catheter reception space 572 therebetween. So configured, during assembly a clinician can insert the catheter proximal end 406 into the reception space 572 to fluidly couple the catheter 400 to the port 100, 200. The coupling can utilize a press-fit as described above, or can utilize an o-ring 574 on the housing 570 in similar configuration as described above with respect to FIG. 43 to provide a compressive force on the catheter 400 and stem 568.

Figure 48:
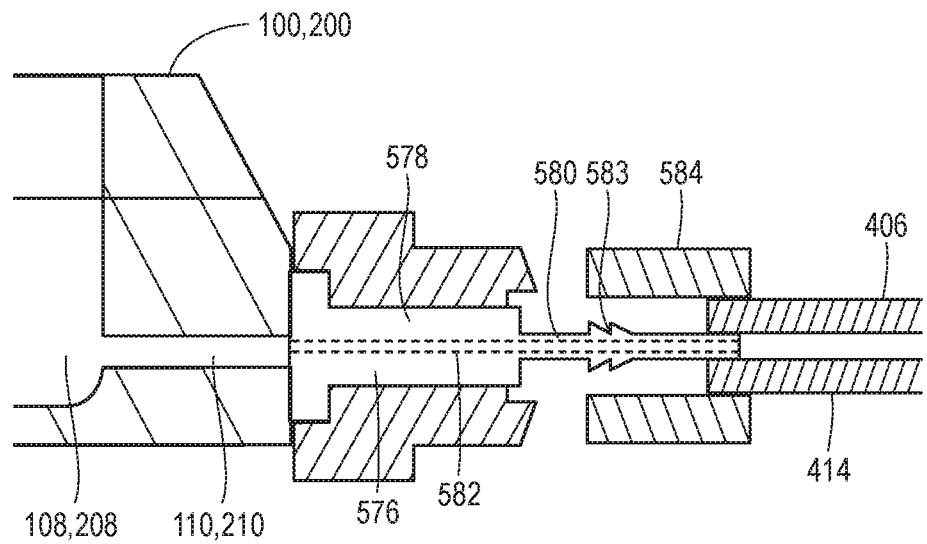
FIG. 48 is a cross-sectional view of a tenth catheter and port connection assembly in accordance with various embodiments.

In another example, as shown in FIG. 48, the port 100, 200 can include a connection member 576 having a base 578 and an outwardly projecting stem 580, which can be made of metal, such as titanium, for example. The connection member 576 includes a passage 582 therethrough that is fluidly coupled to the delivery opening 110, 210. As shown, the stem 580 can include barbs 583 that extend outwardly from an intermediate portion thereof to engage and retain the catheter proximal end 406 after assembly. The assembly 500 of this form can further include a plastic housing 584 extending around the connection member 576 to engage the outer jacket 414 of the catheter 400. So configured, a clinician can insert the catheter proximal end 406 over the stem 580 until the catheter 400 abuts the base 578. The barbs 583 and housing 584 provide a compressive force on the catheter 400 to secure the catheter 400 to the port 100, 200.

Figure 49:
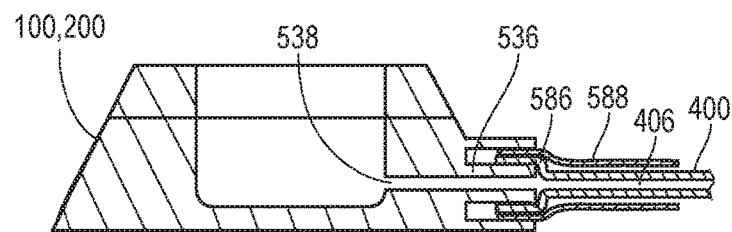
FIG. 49 is a cross-sectional view of an eleventh example catheter and port connection assembly in accordance with various embodiments.

In another example, as shown in FIG. 49, the tube 536 can have an outer diameter that is larger than an inner diameter of the catheter 400 and the catheter proximal end 406 can be flexible to be stretched over the tube 536 during assembly. By one approach, the tube 536 can include a radial lip or barb 586 extending therearound to retain the stretched catheter end 406 on the tube 536. Given the flexible nature of the catheter proximal end 406 of this form, the assembly 500 can further include a rigid or resilient sleeve 588 that extends along the flexible length of the catheter 400 to prevent the flexible portion from becoming kinked.

Figure 50:
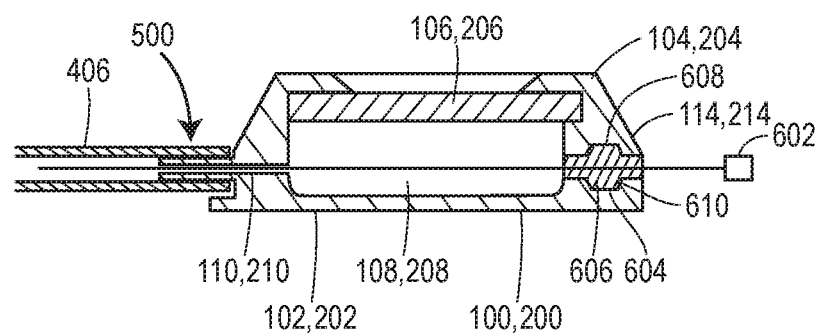
FIG. 50 is a cross-sectional view of an example port for a fluid delivery system having a side septum for a stylet in accordance with various embodiments.

As is understood, implantation of a catheter into the intrathecal space of a patient can be achieved using a stylet. As shown in FIG. 50, the port 100, 200 can include a side septum assembly 600 so that a stylet 602 can be pre-loaded and provided with the port 100, 200. The side septum assembly 600 includes a radial cavity 604 extending between the chamber 108, 208 and the exterior 114, 214 of the body 102, 202 and a septum 606 received within the cavity 604. In the illustrated form, the cavity 604 includes an outwardly projecting recess 608 to receive a flange portion 610 of the septum 606 to prevent or minimize movement of the septum 606 while the style 602 is moved therethrough. The side septum assembly 600 can advantageously be located across the chamber 108, 208 from the delivery opening 110, 210 so that the stylet 602 can be easily threaded therethrough. Further, the side septum assembly 600 can be utilized with any of the catheter connection assemblies 500 described above.

One example method for implanting the fluid delivery systems described herein includes selecting a suitable bony structure of a patient for implantation of the port 100, 200 and securing the port 100, 200 to the bony structure by any suitable method. The method can further include a clinician placing the distal end 408 of the catheter 400 in the intrathecal space of a patient, utilizing the features and properties of the catheter 400 to tunnel the proximal end 406 of the catheter 400 under the skin within the intrathecal space to the subcutaneously implanted port 100, 200, and connecting the catheter 400 to the port 100, 200 via any of the connection assemblies 500 described herein.

After the port 100, 200 and catheter 400 have been implanted and coupled together, a clinician can utilize the fluid delivery system to sample cerebrospinal fluid for diagnostic purposes or can utilize the system to deliver a composition (e.g., a dose of a therapeutic agent) to the intrathecal space of the patient. The clinician can locate the subcutaneous port 100, 200 using any of the above-described features. After the port 100, 200, and the septum 106, 206 thereof, is located a clinician can use a Huber needle attached to a standard syringe containing the composition and, manually, using a standard syringe pump, or using Pulsar auto-injector pump, slowly inject the composition into the chamber 108, 210 to dispense the composition through the outlets 418, 428 of the catheter 400 into the intrathecal space of the patient. The medication can be delivered as bolus or per infusion algorithm from the Pulsar pump using the Pulsar auto-injector pump. In some cases where the composition comprises a therapeutic agent, an approved dosing regimen of the therapeutic agent may require removal of cerebrospinal fluid before injection of the therapeutic agent, which can be done manually, using a standard syringe pump, or using Pulsar auto injector pump from the port 100, 200 via the non-coring Huber needle attached to a syringe. The syringe can also be loaded to a Pulsar auto injector pump.

The port 100, 200, and the chamber 108, 208 thereof, can be configured so that there is minimal dead volume for the composition. For example, the dead volume of the port 100, 200 can be between about 1.0 mL and no dead volume, and, in one form, about 0.5 mL.

Figure 51:
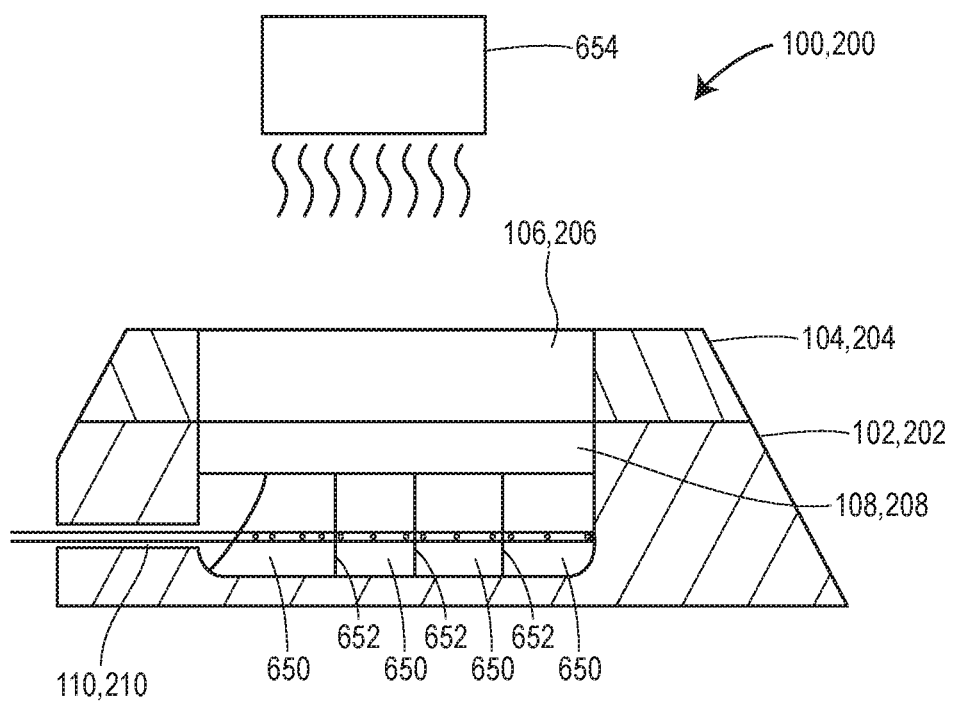
FIG. 51 is a cross-sectional view of an example port for a fluid delivery system being impregnated or pre-loaded with one or more dosages of a medication in accordance with various embodiments.

In another example, as shown in FIG. 51, the chamber 108, 208 of the port 100, 200 can be impregnated or pre-loaded with one or more dosages 650 of a therapeutic agent. A clinician can dispense one of the doses 650 by applying pressure to the septum 106, 206 or other movable portion of the port 100, 200 to force the dose 650 through the delivery opening 110, 210 and into the catheter 400. If more than one dose 650 is provided, the dosages 650 can be separated by movable doors 652 extending across the chamber 108, 208. The doors 652 can be metallic and be selectively and non-invasively moved by a clinician using an external device 654 having one or more magnets therein.

The fluid delivery systems described herein can further be provided as a set, which can include an implantation kit/introducer, anchoring components for the catheter 400, and/or a facial anchor. Further, if desired, a filter can be provided in the catheter, delivery opening 110, 210, or chamber 108, 208.

The device described herein is suitable for administering any fluid composition, such as a pharmaceutical composition comprising one or more therapeutic agents, to a subject. Indeed, the device of the disclosure optionally comprises one or more dosages of a therapeutic agent, such as a therapeutic agent suitable for treating (in whole or in part) a disorder, infection, or injury of the central nervous system or spine. Disorders associated with aspects of the central nervous system or spine include, but are not limited to, spinal muscular atrophy, survival motor neuron deficiency, ankylosing spondylitis, spinal tumors, bipolar disorder, encephalitis, depression, epilepsy, Dravet Syndrome, meningitis, multiple sclerosis, myeopathy, Angelman's Syndrome, CNS lymphoma, Leptomeningeal cancer, Friedreich's Ataxia, hereditary cerebral hemorrhage with amyloidosis-Dutch type (HCHWA-D), cerebral amyloid angiopathy (CAA), amyloid congophilic angiopathy (ACA), and secondary malignant neoplasms (SMN), or neurodegenerative disorders, e.g., Tau protein-related disorders including Alzheimer's disease, Huntington's disease, alpha-synuclei-related disorders including Parkinson's disease, amyotrophic lateral sclerosis (ALS) including superoxide dismutase 1-related ALS, progressive spranuclear palsy, frontotemporal dementia, and Tourette's syndrome. Infections of the CNS include, but are not limited to, viral meningitis, fungal meningitis, epidural infection, viral encephalitis, and neurosyphilis.

Any therapeutic agent may be used in the context of the disclosure. Exemplary therapeutic agents include, e.g., nucleic acids, protein therapeutics, cell therapies, and small molecule therapeutics. Examples of protein therapeutics include antibody-based therapeutics, such as antibodies, antibody fragments, or antibody-like protein products that include binding regions of antibodies (e.g., scFv, diabodies, antibody mimetics, and the like). The antibody-based therapeutic may target, e.g., amyloid plaques, tau proteins, cancer antigens, or abnormal alpha-synuclein. Examples of protein therapeutics also include, but are not limited to, hormones, enzymes (e.g., lysosomal enzymes, such as alpha-L-iduronidase, N-acetylgalactosamine-4-sulfatase, or beta-glucuronidase), growth factors (e.g., fibroblast growth factor (FGF) or neurotrophins or neurotrophic factors, such as glial cell-derived neurotrophic factor (GDNF), brain-derived neurotrophic factor (BDNF), ciliary neurotrophic factor (CNTF), or nerve growth factor (NGF)), blood factors, bone morphogenetic proteins, interferons, interleukins, and thrombolytics. Examples of cell-based therapies include, but are not limited to, stem cell therapeutics and immune cells (including modified immune cells, such as CAR T cells). Suitable small molecule therapeutics include, but are not limited to, analgesics, ion channel blockers, anti-convulsive agents, antibiotics or antiviral agents, anti-inflammatories, anticoagulants, chemotherapeutic, anti-depressants, anti-anxiety agents, steroids, and the like. In various aspects, the therapeutic agent is baclofen, morphine, bupivacaine hydrochloride, clonidine hydrochloride, gabapentin, idursulfase, cytarabine, methotrexate, a corticosteroid, edavarone-conjugate, conotoxin, abomorphine, prednisolone hemisuccinate sodium, carbidopa/levodopa, tetrabenazine, benzodiazepines, such as diazepam and midazolam, alphaxalone or other derivative, cyclophosphamide, idursulfase (Elaprase®), iduronidase (Aldurazyme®), topotecan, buslfan, opmaveloxolone, epicatechin, methylprednisolone, frataxin replacement, reservatrol, nicontinamide, AT-010 (RNA that induces splicing modulation in the mature amyloid precursor protein mRNA), Cerebril™, an anti-Aβ antibody, elenbecestat, a corticosteroid, or nusinersen (Spinraza®), or combinations thereof.

In various aspects, the therapeutic agent is a nucleic acid, including DNA or RNA, which may be single stranded or double stranded and which may be modified or unmodified. Suitable nucleic acid-based therapeutic agents include, but are not limited to, antisense oligonucleotides, ribozymes, miRNA, siRNA, and shRNA. Optionally, the nucleic acid targets a gene selected from the group consisting of APP, MAPT, SOD1, BACE1, CASP3, TGM2, TARDBP, ADRB1, CAMK2A, CBLN1, CDK5R1, GABRA1, MAPK10, NOS1, NPTX2, NRGN, NTS, PDCD2, PDE4D, PENK, SYT1, TTR, FUS, LRDD, CYBA, ATF3, CASP2, HRK, C1QBP, BNIP3, MAPK8, MAPK14, Rac1, GSK3B, P2RX7, TRPM2, PARG, CD38, STEAP4, BMP2, GJA1, TYROBP, CTGF, ANXA2, DUOX1, RTP801, RTP801L, NOX4, NOX1, NOX2 (gp91pho, CYBB), NOX5, DUOX2, NOXO1, NOXO2 (p47phox, NCF1), NOXA1, NOXA2 (p67phox, NCF2), p53 (TP53), HTRA2, KEAP1, SHC1, ZNHIT1, LGALS3, SESN2, SOX9, ASPP1, CTSD, CAPNS1, FAS, FASLG, CAPN1, FADD, CASP1, CASP9, p75NTR, PARK2, HTT (with expanded repeats), NogoA, MAG, OMGP, NgR1, PDE4, BCAN, NCAN, PTPRZ1, TNC, NRP1, NRP2, PLXNA1, PLXNA2, PLXNB1, PLXNC1, TROY, LRRC1, ROCK1, LimK1, LimK2, CFL1, KCNC4, KCNE3, NAT8L, FKBP1A, FKBP4, LRRK2, DYRK1A, AKAP13, UBE2K, WDR33, MYCBP2, SEPHS1, HMGB1, HMGB2, TRPM7, BECN1, THEM4, SLC4A7, MMP9, SLC11A2, ATXN3, ATXN1, ATXN7, PRNP, EFNB3, EPHA4, EFNA5, EPHA7 and EFNB2, such that gene expression or function is modified.

In some embodiments, the therapeutic agent is an oligonucleotide comprising at least one modified nucleotide, optionally a modified nucleotide that reduces binding to cerebral spinal fluid (CSF) proteins. In various embodiments, the modified nucleotide includes a substituent at the 2'-position, such as a 2'-O-2-methoxyethyl ("2'-MOE") group, as shown below, wherein X is O or S.

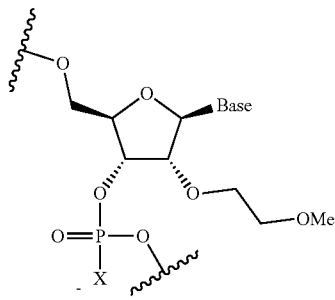

Oligonucleotides comprising a 2'-MOE modification can distribute rapidly in central nervous system tissues. Oligonucleotides comprising such modifications exhibit extended half-lives in CSF and central nervous system tissues, which can result in less frequent dose administration.

In some cases, the modified nucleotide can include a 2',4'-constrained group, such as a constrained 2'-O-ethyl ("cEt") group. In various cases, the cEt group can have S-stereochemistry ("S-cEt"), as shown below, wherein X is O or S.

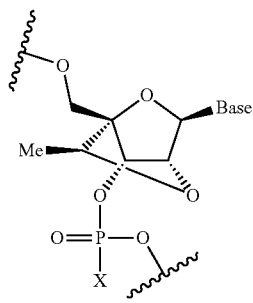

Nucleic acids modified with a constrained ethyl group, such as S-cEt, can exhibit enhanced thermal stability, good potency, and a good therapeutic profile.

Optionally, the nucleic acid encodes a beneficial protein that, e.g., replaces an absent or defective protein, or encodes a cytotoxic protein that achieves a therapeutic effect, such as cancer cell death. Any of the protein-based therapeutics described herein may be delivered to a subject via delivery of a nucleic acid encoding the protein under conditions which allow expression in vivo. For example, in various embodiments, the nucleic acid encodes a neurotrophic factor such as, but not limited to, nerve growth factor (NGF), brain-derived neurotrophic factor (BDNF), neurotrophin-3 (NT-3), neurotrophin-4/5 (NT-4/5), neurotrophin-6 (NT-6), ciliary neurotrophic factor (CNTF), glial cell line-derived neurotrophic factor (GDNF), the fibroblast growth factor family (e.g., FGF's 1-15), leukemia inhibitory factor (LIF), certain members of the insulin-like growth factor family (e.g., IGF-1), a neurturin, persephin, a bone morphogenic protein (BMPs), an immunophilin, a member of the transforming growth factor (TGF) family of growth factors, a neuregulin, epidermal growth factor (EGF), platelet-derived growth factor (PDGF), vascular endothelial growth factor family (e.g. VEGF 165), follistatin, or Hifl, or combinations thereof.

In various aspects, the nucleic acid is present in a viral vector. Any viral vector appropriate for delivering a therapeutic agent to a human subject may be used. Examples of viral vectors include, e.g., herpes simplex virus (HSV) vectors, adenovirus (Ad) vectors, parvoviral-based vectors (e.g., adeno-associated viral vectors), chimeric Ad-AAV vectors, and retroviral vectors (including lentiviral vectors, HIV vectors). Any of these gene transfer vectors can be prepared using standard recombinant DNA techniques described in, e.g., Sambrook et al., Molecular Cloning, a Laboratory Manual, 2d edition, Cold Spring Harbor Press, Cold Spring Harbor, N.Y. (1989), and Ausubel et al., Current Protocols in Molecular Biology, Greene Publishing Associates and John Wiley & Sons, New York, N.Y. (1994).

In some embodiments, the viral vector is an AAV vector. AAV vectors used for administration of a therapeutic nucleic acid typically have approximately 96% of the parental genome deleted, such that only the terminal repeats (ITRs), which contain recognition signals for DNA replication and packaging, remain. Delivering the AAV rep protein enables integration of the AAV vector comprising AAV ITRs into a specific region of genome, if desired. AAV vectors are useful for delivering payload to the central nervous system due, at least in part, to their safety profile, long-term gene expression, and ability to infect both dividing and quiescent cells, including neurons. Multiple serotypes of AAV exist and offer varied tissue tropism. Known serotypes include, for example, AAV1, AAV2, AAV3, AAV4, AAV5, AAV6, AAV7, AAV8, AAV9, AAV10 and AAV11. AAV vectors may be engineered to alter the virus's native tropism or improve infection by modifying the viral capsid or packaging the genome of one serotype into the capsid of a different serotype. AAV vectors have been used to deliver a number of transgenes to treat a variety of diseases, including ASP to treat Canavan disease; CLN2 to treat Late infantile neuronal ceroid lipofuscinosis; SGSH to treat mucopolysaccharidosis IIIA; NAGLU to treat mucopolysaccharidosis IIIB; ARSA to treat metachromatic leukodystrophy; GAD, AADC, NTN, GDNF, AADC to treat Parkinson's; and NGF to treat Alzheimer's. See, e.g., Hocquemiller et al., Hum Gene Ther., 27(7), 478-496 (2016), hereby incorporated by reference. The genomic sequences of AAV, as well as the sequences of the ITRs, Rep proteins, and capsid subunits are known in the art. See, e.g., International Patent Publications Nos. WO 00/28061, WO 99/61601, WO 98/11244; as well as U.S. Pat. No. 6,156,303, Srivistava et al. (1983) J Virol. 45:555; Chiorini et al (1998) J Virol. 71:6823; Xiao et al (1999) J Virol. 73:3994; Shade et al (1986) J Virol. 58:921; and Gao et al (2002) Proc. Nat. Acad. Sci. USA 99:11854.

In various embodiments, the device is used to deliver one or more gene editing agents to a subject, such as the clustered regularly interspaced short palindromic repeats (CRISPR) associated protein (Cas) system. CRISPR-Cas and similar gene targeting systems are in the art with reagents and protocols readily available. See, e.g., Mali et al., Science, 339(6121), 823-826 (2013); and Hsu et al., Cell, 157.6: 1262-1278 (2014). Exemplary genome editing protocols are described in Doudna and Mali, "CRISPR-Cas: A Laboratory Manual" (2016) (CSHL Press, ISBN: 978-1-621821-30-4) and Ran et al., Nature Protocols 8(11): 2281-2308 (2013). The CRISPR/Cas system comprises a CRIPSR/Cas nuclease (typically Cas9) and guide RNA (or crRNA-tracrRNA) comprising a short nucleotide targeting sequence that directs the nuclease to a genome location of interest. The guide RNA(s) and coding sequence for the Cas nuclease, optionally packaged into viral vectors, can be delivered to the CSF via the device of the disclosure. The CRISPR/Cas system is further described in, e.g., U.S. Patent Publication Nos. 2018/0223311.

In various aspects, the disclosure provides a method of treating Huntington's disease, Spinal Muscular Atrophy (SMA), survival motor neuron (SMN) deficiency, amyotrophic lateral sclerosis (ALS) (including superoxide dismutase 1 (SOD1)-related ALS), Angelman's syndrome, Dravet syndrome, Alzheimer's disease and other tau protein-related disorders, progressive supranuclear palsy (PSP), frontotemporal dementia (FTD), alpha-synuclei-related disorders including Parkinson's Disease, central nervous system (CNS) lymphoma, leptomeningeal cancer, Friedreich's Ataxia, hereditary cerebral hemorrhage with amyloidosis-Dutch type (HCHWA-D), cerebral amyloid angiopathy (CAA), amyloid congophilic angiopathy (ACA), or secondary malignant neoplasms (SMN). The method comprises implanting a fluid delivery system in the patient such that a catheter of the fluid delivery system is disposed within the patient's intrathecal space, the catheter characterized by a catheter body having an outer diameter in the range of about 0.25 mm to 1.5 mm and a composite, kink-resistant structure. The fluid delivery system further comprises a grommet having a sleeve portion extending around the catheter body and a flange portion to engage the dura of the patient over a catheter opening therein. The method further comprises releasing a therapeutic agent (such as any one or more of the therapeutic agents described above) via the catheter into the intrathecal space, such that the disorder is treated.

It will be appreciated that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. The same reference numbers may be used to describe like or similar parts. Further, while several examples have been disclosed herein, any features from any examples may be combined with or replaced by other features from other examples. Moreover, while several examples have been disclosed herein, changes may be made to the disclosed examples within departing from the scope of the claims.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A catheter comprising:
a body having a proximal end configured to be fluidly coupled to a port, a distal end, a central passage extending between the proximal end and the distal end, and a distal outlet in the distal end,
wherein the central passage comprises a choked portion adjacent to the distal outlet to create a venturi effect with fluid being dispensed through the distal outlet;
wherein the distal end of the catheter further comprises one or more side passages fluidly coupling the central passage to an exterior of the catheter to draw in fluid from the exterior of the catheter and provide mass flow rate amplification to fluid being dispensed through the distal outlet, the one or more side passages each extending at an angle with respect to a longitudinal axis of the catheter such that interior openings of the one or more side passages are closer to the distal outlet than exterior openings thereof, the interior openings of each of the one or more side passages being disposed downstream of the choked portion;
wherein the distal end of the catheter further comprises a mixing chamber of the central passage disposed distal of the choked portion, the mixing chamber having a larger diameter than the choked portion, and the interior openings of the one or more side passages open into the mixing chamber such that cerebrospinal fluid is configured to be drawn into the central passage of the catheter through the one or more side passages to join the flow of fluid through the choked portion creating a higher mass flow through the distal outlet.

2. A fluid delivery system including the catheter of claim 1, the fluid delivery system further comprising:
a port implantable to a subcutaneous location, the port including a body of the port defining a chamber having an open top and a delivery opening, a septum coupled to the body to extend over the open top of the chamber, and a catheter connection portion for the catheter.

3. The fluid delivery system of claim 2, further comprising:
a grommet configured to couple to a portion of the catheter in between the proximal end and the distal end, and spaced from the port, wherein the catheter is configured to be inserted through a tissue catheter opening extending through the dura and fascia of a patient such that the distal end of the catheter is disposed within the intrathecal space of the patient, and the grommet comprises a body having a sleeve portion formed by an annular wall defining a bore to receive the catheter therethrough and an annular flange portion extending outwardly from an end of the annular wall of the sleeve portion, wherein the annular flange portion is configured to engage the dura of the patient with the bore of the annular wall aligned with the tissue catheter opening when the catheter is inserted therethrough to protect against leakage of cerebrospinal fluid from the tissue catheter opening.

4. The catheter of claim 1, wherein the body further comprises a plurality of radially oriented outlets.

5. The catheter of claim 4, wherein the plurality of radially oriented outlets are disposed along an axial length of the body in a spiral configuration.

6. The catheter of claim 4, wherein the plurality of radially oriented outlets comprise at least one of: one or more rings of outlets disposed within a plane normal to an axial length of the body or a plurality of outlets aligned and spaced from one another along the axial length of the body.

7. The catheter of claim 4, wherein the distal outlet and the plurality of radially oriented outlets are sized so that more fluid volume is dispensed through the distal outlet than through the plurality of radially oriented outlets.

8. The catheter of claim 4, wherein the distal outlet and the plurality of radially oriented outlets are sized so that a fluid volume dispensed through the distal outlet is substantially equal to a fluid volume dispensed through the plurality of radially oriented outlets.

9. The catheter of claim 4, wherein the body includes radiopaque markings at one or more of: adjacent to the distal end, proximal to of the plurality of radially oriented outlets, or distal to the plurality of radially oriented outlets.

10. The catheter of claim 1, wherein the body is radiopaque.

11. The catheter of claim 1, wherein at least a portion of the body has a 3 layer construction including an inner lumen, a reinforcement layer, and an outer jacket.

12. The catheter of claim 1, wherein the distal end comprises an atraumatic tip allowing implantation without damaging or exiting the intrathecal space.

13. The catheter of claim 1, wherein the distal outlet has a smaller diameter than an inner diameter of the central passage adjacent to the distal outlet.

14. The catheter of claim 1, wherein the body has an outer diameter in the range of 0.25 mm to 1.5 mm.

15. The catheter of claim 1, wherein the proximal end of the body comprises a reinforcement material increasing the strength of the proximal end resisting crushing damage from compression, the reinforcement material comprising one or more of: a plurality of rings embedded within the proximal end, a coil embedded within the proximal end, a polymer tube embedded within the proximal end, or a braided material embedded within the proximal end.

16. The catheter of claim 15, wherein the reinforcement material causes the proximal end of the body to include exterior protrusions.

17. The catheter of claim 1, further comprising one or more dosages of a nucleic acid, a protein therapeutic, a cell therapy, a small molecule therapeutic, or a combination thereof.

18. The catheter of claim 17, comprising a nucleic acid selected from the group consisting of an antisense oligonucleotide, a ribozyme, an miRNA, an siRNA, and shRNA, or a nucleic acid encoding a clustered regularly interspaced short palindromic repeats (CRISPR) associated protein (Cas) system, or a combination thereof.

19. The catheter of claim 18, wherein the nucleic acid is an antisense oligonucleotide comprising a 2'-O-2-methoxyethyl ("2'-MOE") group.

20. The catheter of claim 18, comprising an antisense oligonucleotide, and the antisense oligonucleotide is nusinersen.

21. The catheter of claim 18, comprising an antisense nucleic acid that targets the huntingtin gene.

22. The catheter of claim 17, comprising one or more dosages of a viral vector encoding a therapeutic protein.

23. The catheter of claim 22, wherein the viral vector is an adeno-associated viral vector or an adenoviral vector.

24. The catheter of claim 17, wherein the nucleic acid, protein therapeutic, cell therapy, small molecule therapeutic, or combination thereof treats a disorder selected from the group consisting of Huntington's disease, Spinal Muscular Atrophy (SMA), survival motor neuron (SMN) deficiency, amyotrophic lateral sclerosis (ALS), Angelman's Syndrome, Dravet Syndrome, Alzheimer's disease, progressive supranuclear palsy (PSP), frontotemporal dementia (FTD), Parkinson's Disease, central nervous system (CNS) lymphoma, Leptomeningeal Cancer, Friedreich's Ataxia, hereditary cerebral hemorrhage with amyloidosis-Dutch type (HCHWA-D), cerebral amyloid angiopathy (CAA), amyloid congophilic angiopathy (ACA), and secondary malignant neoplasms (SMN).

25. The catheter of claim 1, wherein the distal end has a rounded configuration such that the distal outlet has a smaller diameter than an inner diameter of the mixing chamber of the central passage disposed adjacent thereto.

26. The fluid delivery system of claim 2, further comprising:
a plug configured to couple to the body of the catheter in between of the proximal end and the distal end, and spaced from the port, wherein the catheter is configured to be inserted through a tissue catheter opening extending through the dura and fascia of a patient such that the distal end of the catheter is disposed within the intrathecal space of the patient, and the plug comprises an elongate body having a passage to receive the catheter therethrough, an end of the elongate body being configured to be inserted into the tissue catheter opening through the fascia to abut the dura when the catheter is inserted therethrough to protect against leakage of cerebrospinal fluid from the intrathecal space through the tissue catheter opening.

27. The fluid delivery system of claim 26, wherein the elongate body of the plug has a bent configuration.

28. The fluid delivery system of claim 26, wherein at least one of: the elongate body of the plug includes an external annular recess extending therearound configured to receive tissue of the patient after tightening of a suture; or the plug further comprises one or more tabs extending outwardly from the elongate body having opening extending therethrough for reception of a suture to secure the plug to tissue of the patient.

* * * * *

UNITED STATES PATENT AND TRADEMARK OFFICE
CERTIFICATE OF CORRECTION

PATENT NO. : 10,940,290 B2
APPLICATION NO. : 16/113955
DATED : March 9, 2021
INVENTOR(S) : Deep Arjun Singh et al.

Page 1 of 1

It is certified that error appears in the above-identified patent and that said Letters Patent is hereby corrected as shown below:

In the Claims

At Column 28, Line 34, "between of the" should be -- between the --.

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*